US006338845B1

(12) United States Patent
Terman

(10) Patent No.: US 6,338,845 B1
(45) **Date of Patent: *Jan. 15, 2002**

(54) TUMOR KILLING EFFECTS OF ENTEROTOXINS, SUPERANTIGENS, AND RELATED COMPOUNDS

(76) Inventor: David S. Terman, 3183 Palmero Way, Pebble Beach, CA (US) 93953

( * ) Notice: Subject to any disclaimer, the term of this patent is extended or adjusted under 35 U.S.C. 154(b) by 0 days.

This patent is subject to a terminal disclaimer.

(21) Appl. No.: 09/314,235

(22) Filed: May 18, 1999

Related U.S. Application Data

(63) Continuation of application No. 08/896,933, filed on Jul. 18, 1997, now Pat. No. 6,221,351, which is a division of application No. 08/252,978, filed on Jun. 2, 1994, now Pat. No. 6,126,945, which is a continuation of application No. 07/891,718, filed on Jun. 1, 1992, now abandoned, which is a continuation-in-part of application No. PCT/US91/00342, filed on Jan. 17, 1991, which is a continuation-in-part of application No. 07/466,577, filed on Nov. 17, 1990, now abandoned, which is a continuation-in-part of application No. 07/416,530, filed on Oct. 3, 1989, now abandoned.

(51) Int. Cl.$^7$ ............................ A01N 63/00; C12N 5/08

(52) U.S. Cl. .................. 424/93.1; 424/93.2; 424/93.21; 424/93.7; 424/93.71; 435/372; 435/372.1; 435/372.2; 435/372.3

(58) Field of Search ................................ 435/325, 363, 435/366, 372, 372.1, 372.2, 372.3; 424/93.1, 93.2, 93.21, 93.7, 93.71

*Primary Examiner*—Geetha P. Bansal
(74) *Attorney, Agent, or Firm*—Venable; Shmuel Livnat

(57) ABSTRACT

Superantigens, including staphylococcal enterotoxins, are useful agents for killing tumor cells, enhancing antitumor immunity and treating cancer in a tumor-bearing host. Other useful superantigens include Streptococcal pyrogenic exotoxin, toxic shock syndrome toxins, mycoplasma antigens, mycobacteria antigens, minor lymphocyte stimulating antigens, heat shock proteins, stress peptides and derivatives thereof. The immune system of a subject with cancer is contacted with tumor cells that have been transfected with a nucleic acid encoding a superantigen or biologically active polypeptide of a superantigen. Alternatively, transfected accessory cells, inmunocytes or fibroblasts are used. Expression of the superantigen in the host induces T cell proliferation leading to increased antitumor immunity and tumor cell killing. The superantigen encoding nucleic acid may be administered to the tumor in vivo to transfect tumor cells, wherein superantigen expression induces a tumoricidal immune response. Furthermore, transfected cells incubated ex vivo with an immunocyte population, particularly T lymphocytes, tumoricidally activate the population; such activated cells are then administered to the tumor-bearing host.

30 Claims, No Drawings

SEQUENCE LISTING

<160> NUMBER OF SEQ ID NOS: 34

<210> SEQ ID NO 1
<211> LENGTH: 14
<212> TYPE: PRT
<213> ORGANISM: Staphylococcus aureus

<400> SEQUENCE: 1

Cys Met Tyr Gly Gly Val Thr Leu His Asp Asn Asn Arg Leu
 1               5                   10

<210> SEQ ID NO 2
<211> LENGTH: 17
<212> TYPE: PRT
<213> ORGANISM: Staphylococcus aureus

<400> SEQUENCE: 2

Lys Lys Asn Val Thr Val Gln Glu Leu Asp Leu Gln Ala Arg Arg Tyr
 1               5                   10                  15

Leu

<210> SEQ ID NO 3
<211> LENGTH: 13
<212> TYPE: PRT
<213> ORGANISM: Staphylococcus aureas

<400> SEQUENCE: 3

Cys Met Tyr Gly Gly Val Thr Glu His His Gly Asn Leu
 1               5                   10

<210> SEQ ID NO 4
<211> LENGTH: 17
<212> TYPE: PRT
<213> ORGANISM: Staphylococcus aureas

<400> SEQUENCE: 4

Lys Lys Lys Val Thr Ala Gln Glu Leu Asp Tyr Leu Thr Arg His Tyr
 1               5                   10                  15

Leu

<210> SEQ ID NO 5
<211> LENGTH: 14
<212> TYPE: PRT
<213> ORGANISM: Staphylococcus aureas

<400> SEQUENCE: 5

-continued

```
Cys Met Tyr Gly Gly Ile Thr Lys His Glu Gly Asn His Phe
 1               5                   10


<210> SEQ ID NO 6
<211> LENGTH: 17
<212> TYPE: PRT
<213> ORGANISM: Staphylococcus aureas

<400> SEQUENCE: 6

Lys Lys Ser Val Thr Ala Gln Glu Leu Asp Ile Lys Ala Arg Asn Phe
 1               5                   10                  15

Leu


<210> SEQ ID NO 7
<211> LENGTH: 14
<212> TYPE: PRT
<213> ORGANISM: Staphylococcus aureas

<400> SEQUENCE: 7

Cys Thr Tyr Gly Gly Val Thr Pro His Glu Gly Asn Lys Leu
 1               5                   10


<210> SEQ ID NO 8
<211> LENGTH: 17
<212> TYPE: PRT
<213> ORGANISM: Staphylococcus aureas

<400> SEQUENCE: 8

Lys Lys Asn Val Thr Val Gln Glu Leu Asp Ala Gln Ala Arg Arg Tyr
 1               5                   10                  15

Leu


<210> SEQ ID NO 9
<211> LENGTH: 14
<212> TYPE: PRT
<213> ORGANISM: Staphylococcus aureas

<400> SEQUENCE: 9

Cys Met Tyr Gly Gly Val Thr Leu His Asp Asn Asn Arg Leu
 1               5                   10


<210> SEQ ID NO 10
<211> LENGTH: 17
<212> TYPE: PRT
<213> ORGANISM: Staphylococcus aureas

<400> SEQUENCE: 10

Lys Lys Glu Val Thr Val Gln Glu Leu Asp Leu Gln Ala Arg His Tyr
 1               5                   10                  15

Leu


<210> SEQ ID NO 11
<211> LENGTH: 14
<212> TYPE: PRT
<213> ORGANISM: Streptococcus pyogenes

<400> SEQUENCE: 11

Cys Ile Tyr Gly Gly Val Thr Asn His Glu Gly Asn His Leu
 1               5                   10


<210> SEQ ID NO 12
<211> LENGTH: 17
<212> TYPE: PRT
```

-continued

```
<213> ORGANISM: Streptococcus pyogenes

<400> SEQUENCE: 12

Lys Lys Met Val Thr Ala Gln Glu Leu Asp Tyr Lys Val Arg Lys Tyr
 1               5                  10                  15

Leu


<210> SEQ ID NO 13
<211> LENGTH: 14
<212> TYPE: PRT
<213> ORGANISM: Other
<220> FEATURE:
<223> OTHER INFORMATION: Consensus sequences derived from stapholycoccus
      aureus and streptococcus pyogenes polypeptides

<400> SEQUENCE: 13

Cys Met Tyr Gly Gly Val Thr Leu His Glu Gly Asn His Leu
 1               5                  10


<210> SEQ ID NO 14
<211> LENGTH: 17
<212> TYPE: PRT
<213> ORGANISM: Other
<220> FEATURE:
<223> OTHER INFORMATION: Consensus sequences derived from staphylococcus
      aureus and streptococcus pyogenes polypeptides

<400> SEQUENCE: 14

Lys Lys Asn Val Thr Ala Gln Glu Leu Asp Leu Gln Ala Arg Arg Tyr
 1               5                  10                  15

Leu


<210> SEQ ID NO 15
<211> LENGTH: 17
<212> TYPE: PRT
<213> ORGANISM: Other
<220> FEATURE:
<223> OTHER INFORMATION: Consensus sequences derived from staphylococcus
      aureus and streptococcus  pyogenes polypeptides

<400> SEQUENCE: 15

Lys Lys Asn Val Thr Ala Gln Glu Leu Asp Leu Gln Ala Arg His Tyr
 1               5                  10                  15

Leu


<210> SEQ ID NO 16
<211> LENGTH: 17
<212> TYPE: PRT
<213> ORGANISM: Other
<220> FEATURE:
<223> OTHER INFORMATION: Consensus sequences derived from staphylococcus
      aureus and streptococcus pyogenes polypeptides

<400> SEQUENCE: 16

Lys Lys Asn Val Thr Ala Gln Glu Leu Asp Tyr Gln Ala Arg Arg Tyr
 1               5                  10                  15

Leu


<210> SEQ ID NO 17
<211> LENGTH: 17
<212> TYPE: PRT
<213> ORGANISM: Other
<220> FEATURE:
<223> OTHER INFORMATION: Consensus sequences derived from staphylococcus
      aureus and streptococcus pyogenes polypeptides
```

-continued

<400> SEQUENCE: 17

Lys Lys Asn Val Thr Ala Gln Glu Leu Asp Tyr Gln Ala Arg His Tyr
 1               5                  10                  15

Leu

<210> SEQ ID NO 18
<211> LENGTH: 14
<212> TYPE: PRT
<213> ORGANISM: Staphylococcus aureus

<400> SEQUENCE: 18

Ile His Phe Gln Ile Ser Gly Val Thr Asn Thr Glu Lys Leu
 1               5                  10

<210> SEQ ID NO 19
<211> LENGTH: 17
<212> TYPE: PRT
<213> ORGANISM: Staphylococcus aureas

<400> SEQUENCE: 19

Lys Lys Gln Leu Ala Ile Ser Thr Leu Asp Phe Glu Ile Arg His Gln
 1               5                  10                  15

Leu

<210> SEQ ID NO 20
<211> LENGTH: 220
<212> TYPE: PRT
<213> ORGANISM: Streptococcus pyogenes

<400> SEQUENCE: 20

Ser Thr Arg Pro Lys Pro Ser Gln Leu Gln Arg Ser Asn Leu Val Lys
 1               5                  10                  15

Thr Phe Lys Ile Tyr Ile Phe Phe Met Arg Val Thr Leu Val Thr His
            20                  25                  30

Glu Asn Val Lys Ser Val Asp Gln Leu Leu Ser His Asp Leu Ile Tyr
        35                  40                  45

Asn Val Ser Gly Pro Asn Tyr Asp Lys Leu Lys Thr Glu Leu Lys Asn
    50                  55                  60

Gln Glu Met Ala Thr Leu Phe Lys Asp Lys Asn Val Asp Ile Tyr Gly
65                  70                  75                  80

Val Glu Tyr Tyr His Leu Cys Tyr Leu Cys Glu Asn Ala Glu Arg Ser
                85                  90                  95

Ala Cys Leu Tyr Gly Gly Val Thr Asn His Glu Gly Asn His Leu Glu
            100                 105                 110

Ile Pro Lys Lys Ile Val Val Lys Val Ser Ile Asp Gly Ile Gln Ser
        115                 120                 125

Leu Ser Phe Asp Ile Glu Gln Ile Lys Asn Gly Asn Cys Ser Arg Ile
    130                 135                 140

Ser Tyr Thr Val Arg Lys Tyr Leu Thr Asp Asn Lys Gln Leu Tyr Thr
145                 150                 155                 160

Asn Gly Pro Ser Lys Tyr Glu Thr Gly Tyr Ile Lys Phe Ile Pro Lys
                165                 170                 175

Asn Lys Glu Ser Phe Trp Phe Asp Phe Phe Pro Glu Pro Glu Phe Thr
            180                 185                 190

Gln Ser Lys Tyr Leu Met Ile Tyr Lys Asp Asn Glu Thr Leu Asp Ser
        195                 200                 205

-continued

```
Asn Thr Ser Gln Ile Glu Val Tyr Leu Thr Thr Lys
    210                 215                 220


<210> SEQ ID NO 21
<211> LENGTH: 239
<212> TYPE: PRT
<213> ORGANISM: Staphylococcus aureas

<400> SEQUENCE: 21

Glu Ser Gln Pro Asp Pro Lys Pro Asp Glu Leu His Lys Ser Ser Lys
 1               5                  10                  15

Phe Thr Gly Leu Met Glu Asn Met Lys Val Leu Tyr Asn Asn Asp His
            20                  25                  30

Val Ser Ala Ile Asn Val Lys Ser Ile Asn Glu Phe Phe Asp Leu Ile
        35                  40                  45

Tyr Leu Tyr Ser Ile Lys Asp Thr Lys Leu Gly Asn Tyr Asp Asn Val
    50                  55                  60

Arg Val Glu Phe Lys Asn Lys Asp Leu Ala Asp Lys Tyr Lys Asp Lys
65                  70                  75                  80

Tyr Val Asp Val Phe Gly Ala Asn Tyr Tyr Gln Cys Tyr Phe Ser Lys
                85                  90                  95

Lys Thr Asn Asn Ile Asp Ser His Glu Asn Thr Lys Arg Lys Thr Cys
            100                 105                 110

Met Tyr Gly Gly Val Thr Glu His Gly Asn Asn Gln Leu Asp Lys Tyr
        115                 120                 125

Tyr Arg Ser Ile Thr Val Arg Val Phe Glu Asp Gly Lys Asn Leu Leu
    130                 135                 140

Ser Phe Asp Val Gln Thr Asn Lys Lys Lys Val Thr Ala Glu Gln Leu
145                 150                 155                 160

Asp Tyr Leu Thr Arg His Tyr Leu Val Lys Asn Lys Lys Leu Tyr Glu
                165                 170                 175

Phe Asn Asn Ser Pro Tyr Glu Thr Gly Tyr Ile Lys Phe Ile Glu Asn
            180                 185                 190

Glu Asn Ser Phe Trp Tyr Asp Met Met Pro Ala Pro Gly Asn Lys Phe
        195                 200                 205

Asp Gln Ser Lys Tyr Leu Met Met Tyr Asn Asn Asp Lys Met Val Asp
    210                 215                 220

Ser Lys Asp Val Lys Ile Glu Val Tyr Leu Thr Thr Lys Lys Lys
225                 230                 235


<210> SEQ ID NO 22
<211> LENGTH: 28
<212> TYPE: PRT
<213> ORGANISM: Other
<220> FEATURE:
<223> OTHER INFORMATION: Synthetic sequences derived from staphylococcus
      aureus polypeptides

<400> SEQUENCE: 22

Ser Glu Lys Ser Glu Glu Ile Asn Glu Lys Cys Ala Gly Gly Tyr Pro
 1               5                  10                  15

Asn Lys Thr Ala Cys Met Tyr Gly Gly Val Thr Lys
            20                  25


<210> SEQ ID NO 23
<211> LENGTH: 232
<212> TYPE: PRT
<213> ORGANISM: Staphylococcus aureas
```

-continued

<400> SEQUENCE: 23

```
Ser Glu Lys Ser Glu Glu Ile Asn Glu Lys Asp Leu Arg Lys Lys Ser
 1               5                  10                  15

Glu Leu Gln Gly Thr Ala Leu Gly Asn Leu Lys Gln Ile Tyr Tyr Tyr
            20                  25                  30

Asn Glu Lys Ala Lys Thr Glu Asn Lys Glu Ser His Asp Gln Phe Leu
        35                  40                  45

His Thr Ile Leu Phe Lys Gly Phe Phe Thr Asp His Ser Trp Tyr Asn
    50                  55                  60

Asp Leu Leu Val Asp Phe Asp Ser Lys Asp Ile Val Asp Lys Tyr Lys
65                  70                  75                  80

Gly Lys Lys Val Asp Leu Tyr Gly Ala Tyr Tyr Gly Tyr Gln Cys Ala
                85                  90                  95

Gly Gly Thr Pro Asn Lys Thr Ala Cys Met Tyr Gly Gly Val Thr Leu
            100                 105                 110

His Asp Asn Asn Arg Leu Thr Glu Glu Lys Lys Val Pro Ile Asn Leu
        115                 120                 125

Trp Leu Asp Gly Lys Gln Asn Thr Val Pro Leu Glu Thr Val Lys Thr
    130                 135                 140

Asn Lys Lys Asn Val Thr Val Gln Glu Leu Asp Pro Gln Ala Arg Arg
145                 150                 155                 160

Tyr Leu Gln Glu Lys Tyr Asn Leu Tyr Asn Ser Asp Val Phe Asp Gly
                165                 170                 175

Lys Val Gln Arg Gly Leu Ile Val Phe His Thr Ser Thr Glu Pro Ser
            180                 185                 190

Val Asn Tyr Asp Leu Phe Gly Ala Gln Gly Gln Tyr Ser Asn Thr Leu
        195                 200                 205

Leu Arg Ile Tyr Arg Asp Asn Lys Thr Ile Asn Ser Glu Asn Met His
    210                 215                 220

Ile Asp Ile Tyr Leu Tyr Thr Ser
225                 230
```

<210> SEQ ID NO 24
<211> LENGTH: 226
<212> TYPE: PRT
<213> ORGANISM: Staphylococcus aureas

<400> SEQUENCE: 24

```
Ser Glu Glu Ile Asn Glu Lys Asp Leu Arg Lys Lys Ser Glu Leu Gln
 1               5                  10                  15

Arg Asn Ala Leu Ser Asn Leu Arg Gln Ile Tyr Tyr Tyr Asn Glu Lys
            20                  25                  30

Ala Ile Thr Glu Asn Lys Glu Ser Asp Asp Gln Phe Leu Glu Asn Thr
        35                  40                  45

Leu Leu Phe Lys Gly Phe Phe Thr Gly His Pro Trp Tyr Asn Asp Leu
    50                  55                  60

Leu Val Asp Lys Gly Ser Lys Asp Ala Thr Asn Lys Tyr Lys Gly Lys
65                  70                  75                  80

Lys Val Asp Leu Tyr Gly Ala Tyr Tyr Gly Tyr Gln Cys Ala Gly Gly
                85                  90                  95

Thr Pro Asn Lys Thr Ala Cys Met Tyr Gly Gly Val Thr Leu His Asp
            100                 105                 110

Asn Asn Arg Leu Thr Glu Glu Val Asx Lys Trp Ile Asp Gly Lys Gln
        115                 120                 125
```

-continued

```
Thr Thr Val Pro Ile Asp Lys Val Lys Thr Ser Lys Lys Glu Val Thr
    130                 135                 140

Val Gln Glu Leu Asp Leu Gln Ala Arg His Tyr Leu His Gly Lys Phe
145                 150                 155                 160

Gly Leu Tyr Asn Ser Asp Ser Phe Gly Gly Lys Val Gln Arg Gly Leu
                165                 170                 175

Ile Val Phe His Ser Ser Glu Gly Ser Thr Val Ser Tyr Asp Leu Phe
            180                 185                 190

Asp Ala Gln Gly Gln Tyr Pro Asp Thr Leu Leu Arg Ile Tyr Arg Asp
        195                 200                 205

Asn Lys Thr Ile Asn Ser Glu Asn Met His Ile Asp Ile Tyr Leu Tyr
    210                 215                 220

Thr Thr
225


<210> SEQ ID NO 25
<211> LENGTH: 228
<212> TYPE: PRT
<213> ORGANISM: Staphylococcus aureas

<400> SEQUENCE: 25

Ser Val Lys Glu Lys Glu Leu His Lys Lys Ser Glu Leu Ser Ser Thr
 1               5                  10                  15

Ala Leu Asn Asn Met Lys His Ser Tyr Ala Asp Lys Asn Pro Ile Ile
            20                  25                  30

Gly Glu Asn Lys Ser Thr Gly Asp Gln Phe Leu Glu Asn Thr Leu Leu
        35                  40                  45

Tyr Lys Lys Phe Phe Thr Asp Leu Ile Asn Phe Glu Asp Leu Leu Ile
    50                  55                  60

Asn Phe Asn Ser Lys Glu Met Ala Gln His Phe Lys Ser Lys Asn Val
65                  70                  75                  80

Asp Val Tyr Pro Ile Arg Tyr Ser Ile Asn Cys Tyr Gly Gly Glu Ile
                85                  90                  95

Asp Arg Thr Ala Cys Thr Tyr Gly Gly Val Thr Pro His Glu Gly Asn
            100                 105                 110

Lys Leu Lys Glu Arg Lys Lys Ile Pro Ile Asn Leu Trp Ile Asn Gly
        115                 120                 125

Val Gln Lys Glu Val Ser Leu Asp Lys Val Gln Thr Asp Lys Lys Asn
    130                 135                 140

Val Thr Val Gln Glu Leu Asp Ala Gln Ala Arg Arg Tyr Leu Gln Lys
145                 150                 155                 160

Asp Leu Lys Leu Tyr Asn Asn Asp Thr Leu Gly Gly Lys Ile Gln Arg
                165                 170                 175

Gly Lys Ile Glu Phe Asp Ser Ser Asp Gly Ser Lys Val Ser Tyr Asp
            180                 185                 190

Leu Phe Asp Val Lys Gly Asp Phe Pro Glu Lys Gln Leu Arg Ile Tyr
        195                 200                 205

Ser Asp Asn Lys Thr Leu Ser Thr Glu His Leu His Ile Asp Ile Tyr
    210                 215                 220

Leu Tyr Glu Lys
225


<210> SEQ ID NO 26
<211> LENGTH: 239
<212> TYPE: PRT
<213> ORGANISM: Staphylococcus aureas
```

-continued

<400> SEQUENCE: 26

```
Glu Ser Gln Pro Asp Pro Lys Pro Asp Glu Leu His Lys Ser Ser Lys
 1               5                  10                  15

Phe Thr Gly Leu Met Glu Asn Met Lys Val Leu Tyr Asp Asp Asn His
            20                  25                  30

Val Ser Ala Ile Asn Val Lys Ser Ile Asp Gln Phe Leu Tyr Phe Asp
        35                  40                  45

Leu Ile Tyr Ser Ile Lys Asp Thr Lys Leu Gly Asn Tyr Asp Asn Val
    50                  55                  60

Arg Val Glu Phe Lys Asn Lys Asp Leu Ala Asp Lys Tyr Lys Asp Lys
65                  70                  75                  80

Tyr Val Asp Val Phe Gly Ala Asn Tyr Tyr Tyr Gln Cys Tyr Phe Ser
                85                  90                  95

Lys Lys Thr Asn Asp Ile Asn Ser His Gln Thr Asp Lys Arg Lys Thr
            100                 105                 110

Cys Met Tyr Gly Gly Val Thr Glu His Asn Gly Asn Gln Leu Asp Lys
        115                 120                 125

Tyr Arg Ser Leu Thr Val Arg Val Phe Glu Asp Gly Lys Asn Leu Leu
    130                 135                 140

Ser Phe Asp Val Gln Thr Asn Lys Lys Lys Val Thr Ala Gln Glu Leu
145                 150                 155                 160

Asp Tyr Leu Thr Arg His Tyr Leu Val Lys Asn Lys Lys Leu Tyr Glu
                165                 170                 175

Phe Asn Asn Ser Pro Tyr Glu Thr Gly Tyr Ile Lys Phe Ile Glu Asn
            180                 185                 190

Glu Asn Ser Phe Trp Tyr Asp Leu Met Pro Ala Pro Gly Asp Lys Phe
        195                 200                 205

Asp Gln Ser Lys Tyr Leu Met Asn Tyr Asn Asp Asn Lys Met Val Asp
    210                 215                 220

Ser Lys Asp Val Lys Ile Glu Val Tyr Leu Thr Tyr Lys Lys Lys
225                 230                 235
```

<210> SEQ ID NO 27
<211> LENGTH: 239
<212> TYPE: PRT
<213> ORGANISM: Staphylococcus aureas

<400> SEQUENCE: 27

```
Glu Ser Gln Pro Asp Pro Thr Pro Asp Glu Leu His Lys Ala Ser Lys
 1               5                  10                  15

Phe Thr Gly Leu Met Glu Asn Met Lys Val Leu Tyr Asp Asp His Tyr
            20                  25                  30

Val Ser Ala Thr Lys Val Lys Ser Val Asp Lys Phe Leu Ala His Asp
        35                  40                  45

Leu Ile Tyr Asn Ile Ser Asp Lys Lys Leu Lys Asn Tyr Asp Lys Val
    50                  55                  60

Lys Thr Glu Leu Leu Asn Glu Gly Leu Ala Lys Lys Tyr Lys Asp Glu
65                  70                  75                  80

Val Val Asp Val Tyr Gly Ser Asn Tyr Tyr Val Asn Cys Tyr Phe Ser
                85                  90                  95

Ser Lys Asp Asn Val Gly Lys Val Thr Gly Gly Lys Thr Cys Met Tyr
            100                 105                 110

Gly Gly Ile Thr Lys His Glu Gly Asn His Phe Asp Asn Gly Asn Leu
        115                 120                 125
```

-continued

```
Gln Asn Val Leu Ile Arg Val Tyr Glu Asn Lys Arg Asn Thr Ile Ser
    130                 135                 140

Phe Glu Val Gln Thr Asp Lys Lys Ser Val Thr Ala Gln Glu Leu Asp
145                 150                 155                 160

Ile Lys Ala Arg Asn Phe Leu Ile Asn Lys Lys Asn Leu Tyr Glu Phe
                165                 170                 175

Asn Ser Ser Pro Tyr Glu Thr Gly Tyr Ile Lys Phe Ile Glu Asn Asn
            180                 185                 190

Gly Asn Thr Phe Trp Tyr Asp Leu Met Pro Ala Pro Gly Asp Lys Phe
        195                 200                 205

Asp Gln Ser Lys Tyr Leu Met Met Tyr Asn Asp Asn Lys Thr Val Asp
    210                 215                 220

Ser Lys Ser Val Lys Ile Glu Val His Leu Thr Thr Lys Asn Gly
225                 230                 235


<210> SEQ ID NO 28
<211> LENGTH: 238
<212> TYPE: PRT
<213> ORGANISM: Staphylococcus aureas

<400> SEQUENCE: 28

Ser Gln Pro Asp Pro Thr Pro Asp Glu Leu His Lys Ser Ser Glu Phe
 1               5                  10                  15

Thr Gly Thr Met Gly Asn Met Lys Tyr Leu Tyr Asp Asp His Tyr Val
            20                  25                  30

Ser Ala Thr Lys Val Met Ser Val Asp Lys Phe Leu Ala His Asp Leu
        35                  40                  45

Ile Tyr Asn Ile Ser Asp Lys Lys Leu Lys Asn Tyr Asp Lys Val Lys
    50                  55                  60

Thr Glu Leu Leu Asn Glu Asp Leu Ala Lys Lys Tyr Lys Asp Glu Val
65                  70                  75                  80

Val Asp Val Tyr Gly Ser Asn Tyr Tyr Val Asn Cys Tyr Phe Ser Ser
                85                  90                  95

Lys Asp Asn Val Gly Lys Val Thr Gly Gly Lys Thr Cys Met Tyr Gly
            100                 105                 110

Gly Ile Thr Lys His Glu Gly Asn His Phe Asp Asn Gly Asn Leu Gln
        115                 120                 125

Asn Val Leu Ile Arg Val Tyr Glu Asn Lys Arg Asn Thr Ile Ser Phe
    130                 135                 140

Glu Val Gln Thr Asp Lys Lys Ser Val Thr Ala Gln Glu Leu Asp Ile
145                 150                 155                 160

Lys Ala Arg Asn Phe Leu Ile Asn Lys Lys Asn Leu Tyr Glu Phe Asn
                165                 170                 175

Ser Ser Pro Tyr Glu Thr Gly Tyr Ile Lys Phe Ile Glu Asn Asn Gly
            180                 185                 190

Asn Thr Phe Trp Tyr Asp Leu Met Pro Ala Pro Gly Asp Lys Phe Asp
        195                 200                 205

Gln Ser Lys Tyr Leu Met Met Tyr Asn Asp Asn Lys Thr Val Asp Ser
    210                 215                 220

Lys Ser Val Lys Ile Glu Val His Leu Thr Thr Lys Asn Gly
225                 230                 235


<210> SEQ ID NO 29
<211> LENGTH: 221
<212> TYPE: PRT
```

-continued

<213> ORGANISM: Streptococcus pyogenes

<400> SEQUENCE: 29

Gln Gln Asp Pro Asp Pro Ser Gln Leu His Arg Ser Ser Leu Val Lys
1 5 10 15

Asn Leu Gln Asn Ile Tyr Phe Leu Tyr Glu Gly Asp Pro Val Thr His
20 25 30

Glu Asn Val Lys Ser Val Asp Gln Leu Leu Ser His Asp Leu Ile Tyr
35 40 45

Asn Val Ser Gly Pro Asn Tyr Asp Lys Leu Lys Thr Glu Leu Lys Asn
50 55 60

Gln Glu Met Ala Thr Leu Phe Lys Asp Lys Asn Val Asp Ile Tyr Gly
65 70 75 80

Val Glu Tyr Tyr His Leu Cys Tyr Leu Cys Glu Asn Ala Glu Arg Ser
85 90 95

Ala Cys Ile Tyr Gly Gly Val Thr Asn His Glu Gly Asn His Leu Glu
100 105 110

Ile Pro Lys Lys Ile Val Val Lys Val Ser Ile Asp Gly Ile Gln Ser
115 120 125

Leu Ser Phe Asp Ile Glu Thr Asn Lys Lys Met Val Thr Ala Gln Glu
130 135 140

Leu Asp Tyr Lys Val Arg Lys Tyr Leu Thr Asp Asn Lys Gln Leu Tyr
145 150 155 160

Thr Asn Gly Pro Ser Lys Tyr Glu Thr Gly Tyr Ile Lys Phe Ile Pro
165 170 175

Lys Asn Lys Glu Ser Phe Trp Phe Asp Leu Phe Pro Glu Pro Glu Phe
180 185 190

Thr Gln Ser Lys Tyr Leu Met Ile Tyr Lys Asp Asn Glu Thr Leu Asp
195 200 205

Ser Asn Thr Ser Gln Ile Glu Val Tyr Leu Thr Thr Lys
210 215 220

<210> SEQ ID NO 30
<211> LENGTH: 208
<212> TYPE: PRT
<213> ORGANISM: Streptococcus pyogenes

<400> SEQUENCE: 30

Asp Ser Lys Lys Asp Ile Ser Asn Val Lys Ser Asp Leu Leu Tyr Ala
1 5 10 15

Tyr Thr Ile Thr Pro Tyr Asp Tyr Lys Asp Cys Arg Val Asn Phe Ser
20 25 30

Thr Thr His Thr Leu Asn Ile Asp Thr Gln Lys Tyr Arg Gly Lys Asp
35 40 45

Tyr Tyr Ile Ser Ser Glu Met Ser Tyr Glu Ala Ser Gln Lys Phe Lys
50 55 60

Arg Asp Asp His Val Asp Val Phe Gly Leu Phe Tyr Ile Leu Asn Ser
65 70 75 80

His Thr Gly Glu Tyr Ile Tyr Gly Gly Ile Thr Pro Ala Gln Asn Asn
85 90 95

Lys Val Asn His Lys Leu Leu Gly Asn Leu Phe Ile Ser Gly Glu Ser
100 105 110

Gln Gln Asn Leu Asn Asn Lys Ile Ile Leu Glu Lys Asp Ile Val Thr
115 120 125

Phe Gln Glu Ile Asp Phe Lys Ile Arg Lys Tyr Leu Met Asp Asn Tyr

-continued

```
    130                 135                 140

Lys Ile Tyr Asp Ala Thr Ser Pro Tyr Val Ser Gly Arg Ile Glu Ile
145                 150                 155                 160

Gly Thr Lys Asp Gly Lys His Glu Gln Ile Asp Leu Phe Asp Ser Pro
                165                 170                 175

Asn Glu Gly Thr Arg Ser Asp Ile Phe Ala Lys Tyr Lys Asp Asn Arg
            180                 185                 190

Ile Ile Asn Met Lys Asn Phe Ser His Phe Asp Ile Tyr Leu Glu Lys
        195                 200                 205


<210> SEQ ID NO 31
<211> LENGTH: 193
<212> TYPE: PRT
<213> ORGANISM: Staphylococcus aureas

<400> SEQUENCE: 31

Ser Thr Asn Asp Asn Ile Lys Asp Leu Leu Asp Trp Tyr Ser Ser Gly
 1               5                  10                  15

Ser Asp Thr Phe Ser Asn Ser Glu Val Leu Asp Asn Ser Leu Gly Ser
            20                  25                  30

Met Arg Ile Lys Asn Thr Asp Gly Ser Ile Ser Leu Ile Ile Phe Pro
        35                  40                  45

Ser Pro Tyr Tyr Ser Pro Ala Phe Thr Lys Gly Glu Lys Val Asp Leu
    50                  55                  60

Asn Thr Lys Arg Thr Lys Lys Ser Gln His Thr Ser Glu Gly Thr Tyr
65                  70                  75                  80

Ile His Phe Gln Ile Ser Gly Val Thr Asn Thr Glu Lys Leu Pro Thr
                85                  90                  95

Pro Ile Glu Leu Pro Leu Lys Val Lys Val His Gly Lys Asp Ser Pro
            100                 105                 110

Leu Lys Tyr Gly Pro Lys Phe Asp Lys Lys Gln Leu Ala Ile Ser Thr
        115                 120                 125

Leu Asp Phe Glu Ile Arg His Gln Leu Thr Gln Ile His Gly Leu Tyr
    130                 135                 140

Arg Ser Ser Asp Lys Thr Gly Gly Tyr Trp Lys Ile Thr Met Asn Asp
145                 150                 155                 160

Gly Ser Thr Tyr Gln Ser Asp Leu Ser Lys Phe Glu Tyr Asn Thr Glu
                165                 170                 175

Lys Pro Pro Ile Asn Ile Asp Glu Ile Lys Thr Ile Glu Ala Glu Ile
            180                 185                 190

Asn


<210> SEQ ID NO 32
<211> LENGTH: 241
<212> TYPE: PRT
<213> ORGANISM: Staphylococcus aureas

<400> SEQUENCE: 32

Glu Val Ser Ala Glu Glu Ile Lys Lys His Glu Glu Lys Trp Asn Lys
 1               5                  10                  15

Tyr Tyr Gly Val Asn Ala Phe Asn Leu Pro Lys Glu Leu Phe Ser Lys
            20                  25                  30

Val Asp Glu Lys Asp Arg Gln Lys Tyr Pro Tyr Asn Thr Ile Gly Asn
        35                  40                  45

Val Phe Val Lys Gly Thr Ser Ala Thr Gly Val Leu Ile Gly Lys Asn
    50                  55                  60
```

-continued

```
Thr Val Leu Thr Asn Arg His Ile Ala Lys Phe Ala Asn Gly Asp Pro
65                  70                  75                  80

Ser Lys Val Ser Phe Arg Pro Ser Ile Asn Thr Asp Asp Asn Gly Asn
                85                  90                  95

Thr Glu Thr Pro Tyr Gly Glu Tyr Glu Val Lys Glu Ile Leu Gln Glu
            100                 105                 110

Pro Phe Gly Ala Gly Val Asp Leu Ala Leu Ile Arg Leu Lys Pro Asp
        115                 120                 125

Gln Asn Gly Val Ser Leu Gly Asp Lys Ile Ser Pro Ala Lys Ile Gly
    130                 135                 140

Thr Ser Asn Asp Leu Lys Asp Gly Asp Lys Leu Glu Leu Ile Gly Tyr
145                 150                 155                 160

Pro Phe Asp His Lys Val Asn Gln Met His Arg Ser Glu Ile Glu Leu
                165                 170                 175

Thr Thr Leu Ser Arg Gly Leu Arg Tyr Tyr Gly Phe Thr Val Pro Gly
            180                 185                 190

Asn Ser Gly Ser Gly Ile Phe Asn Ser Asn Gly Glu Leu Val Gly Ile
        195                 200                 205

His Ser Ser Lys Val Ser His Leu Asp Arg Glu His Gln Ile Asn Tyr
    210                 215                 220

Gly Val Gly Ile Gly Asn Tyr Val Lys Arg Ile Ile Asn Glu Lys Asn
225                 230                 235                 240

Glu


<210> SEQ ID NO 33
<211> LENGTH: 246
<212> TYPE: PRT
<213> ORGANISM: Staphylococcus aureas

<400> SEQUENCE: 33

Lys Glu Tyr Ser Ala Glu Glu Ile Arg Lys Leu Lys Gln Lys Phe Glu
 1               5                  10                  15

Val Pro Pro Thr Asp Lys Glu Leu Tyr Thr His Ile Thr Asp Asn Ala
            20                  25                  30

Arg Ser Pro Tyr Asn Ser Val Gly Thr Val Phe Val Lys Gly Ser Thr
        35                  40                  45

Leu Ala Thr Gly Val Leu Ile Gly Lys Asn Thr Ile Val Thr Asn Tyr
    50                  55                  60

His Val Ala Arg Glu Ala Ala Lys Asn Pro Ser Asn Ile Ile Phe Thr
65                  70                  75                  80

Pro Ala Gln Asn Arg Asp Ala Glu Lys Asn Glu Phe Pro Thr Pro Tyr
                85                  90                  95

Gly Lys Phe Glu Ala Glu Glu Ile Lys Glu Ser Pro Tyr Gly Gln Gly
            100                 105                 110

Leu Asp Leu Ala Ile Ile Lys Leu Lys Pro Asn Glu Lys Gly Glu Ser
        115                 120                 125

Ala Gly Asp Leu Ile Gln Pro Ala Asn Ile Pro Asp His Ile Asp Ile
    130                 135                 140

Gln Lys Gly Asp Lys Tyr Ser Leu Leu Gly Tyr Pro Tyr Asn Tyr Ser
145                 150                 155                 160

Ala Tyr Ser Leu Tyr Gln Ser Gln Ile Glu Met Phe Asn Asp Ser Gln
                165                 170                 175

Tyr Phe Gly Tyr Thr Glu Val Gly Asn Ser Gly Ser Gly Ile Phe Asn
            180                 185                 190
```

-continued

```
Leu Lys Gly Glu Leu Ile Gly Ile His Ser Gly Lys Gly Gly Gln Met
        195                 200                 205

Asn Leu Pro Ile Gly Val Phe Phe Asn Arg Lys Ile Ser Ser Leu Tyr
    210                 215                 220

Ser Val Asp Asn Thr Phe Gly Asp Thr Leu Gly Asn Asp Leu Lys Lys
225                 230                 235                 240

Arg Ala Lys Leu Asp Lys
                245


<210> SEQ ID NO 34
<211> LENGTH: 27
<212> TYPE: PRT
<213> ORGANISM: Staphylococcal

<400> SEQUENCE: 34

Ser Glu Lys Ser Glu Glu Ile Asn Glu Lys Asp Leu Arg Lys Lys Ser
 1               5                  10                  15

Glu Leu Gln Gly Thr Ala Leu Gly Asn Leu Lys
            20                  25
```

TUMOR KILLING EFFECTS OF ENTEROTOXINS, SUPERANTIGENS, AND RELATED COMPOUNDS

RELATED APPLICATION DATA

This application is a continuation of U.S. application Ser. No. 08/896,933, filed Jul. 18, 1997 now U.S. Pat. No. 6,221,351, which is a divisional of U.S. application Ser. No. 08/252,978, filed Jun. 2, 1994 now U.S. Pat. No. 6,126,945; which is a continuation of U.S. application Ser. No. 07/891,718, filed Jun. 1, 1992 (abandoned); which is a continuation-in-part of Ser. No. PCT/US91/00342, filed Jan. 17, 1991; which is a continuation-in-part of U.S. application Ser. No. 07/466,577, filed Jan. 17, 1990 (abandoned); which is a continuation-in-part of U.S. application Ser. No. 07/416,530, filed Oct. 3, 1989 (abandoned).

TECHNICAL FIELD

This invention relates generally to tumoricidal compositions and methods, and more specifically to superantigens or enterotoxins derived from *Staphlococcus aureus*. Peptides homologous to the enterotoxins including toxic shock syndrome toxin (TSST-1), Streptococcal pyrogenic exotoxins, mycoplasma and mycobacterial species, minor lymphocyte stimulating antigens, heat shock proteins, stress peptides, mammary tumor virus peptides, homologous synthetic polypeptides, biochemically derivatized enterotoxins, genetically engineered enterotoxins and fusion proteins are also described in this application.

This invention also relates to enterotoxins and homologous compounds known as superantigens expressed on the surface of lipid droplets (in adjuvant-vehicle formulations) or expressed on biologic cell surfaces as a result of enterotoxin gene transfection and used to produde a tumoricidal response in a tumor bearing host. This invention also relates to enterotoxins and related compounds administered intravenously, subcutaneously, as in adjuvant form, or used extracorporeally in free or bound form to stimulate immunocytes which are subsequently infused into tumor bearing hosts.

BACKGROUND OF THE INVENTION

Therapy of the neoplastic diseases has largely involved the use of chemotherapeutic agents, radiation and surgery. However, results with these measures, while beneficial in some tumors, has had only marginal or no effect in many others, while demonstrating unacceptable toxicity. Hence, there has been a quest for newer modalities to treat neoplastic diseases.

In 1980, tumoricidal effects were demonstrated in four of five patients with advanced breast cancer utilizing therapy with plasma perfused over Staphylococcal Protein A. Terman, D. S., Young, J. B., Shearer, W. T., Ayus, C., Lehane, D., Hattioli, C., Espada, R., Howell, J. F., Yamamoto, T., Zaleski, H. E., Miller, L., Frommer, P., Feldman, L., Henry, J. F., Tillquist, R., Cook, G., Daskal, Y., New Eng. J. Med., 305, 1195, 1981. This elaborate system involved the administration of patient plasma which was perfused over a solid surface to which Staphylococcal Protein A was chemically attached. Protein A was prepared by batch fermentation of staphylococcus. It was isolated from the media and partially purified by affinity chromatography.

While the initial observations of tumor killing effects with the immobilized Protein A perfusion system have been confirmed, additional results have been inconsistent. The explanation of these inconsistencies appears to be as follows. First, commercial Protein A has been shown to be an impure preparation, as evident from polyacrylamide gel electrophoresis and radioimmunoassays showing staphylococcal enterotoxins to be present. Secondly, various methods of the immobilization of Protein A to solid supports have been used, sometimes resulting in loss of biological activity of the plasma perfusion system. Thirdly, the plasma used for perfusion over the immobilized Protein A has been stored and treated in different ways, sometimes resulting in inactivation of the system. Moreover, the antitumor element present in this extremely complex perfusion system has not been previously defined. The system contained an enormous number of biologically active materials, to include Staphylococcal Protein A itself, Staphylococcal proteases, nucleases, exotoxins, enterotoxins and leukocidin, as well as the solid support and coating materials. Additional products included several anaphylatoxins generated in plasma after contact with immobilized Protein A. Finally, it is speculated that the biological activity of the system was due to extraction by Protein A of immunosuppressive immune complexes capable of blocking the host's antitumor response.

The present invention demonstrates that isolated Staphylococcal enterotoxins, identified initially as trace contaminants in commercial Protein A preparations can reliably reproduce the tumoricidal reactions and toxicity observed with the whole perfusion system. As such, these materials appear to represent the most active tumoricidal components in the Protein A perfusion system matrix. These materials demonstrate tumoricidal activity in small doses and produce tumoricidal effuse and toxicity identical to that observed in animals and man with the whole Protein A perfusion system. However, the tumoricidal effects may be produced by a simple intravenous injection. Therefore, it has been possible to completely eliminate the elaborate and complex Protein A perfusion system, with its enormous number of component parts, unpredictable performance and potential toxicity problems. This system may be replaced by the enterotoxins which may be administered via simple intravenous injection and have the distinct advantages of convenience, reliability, safety and efficacy over the cumbersome, inefficient and often ineffective extracorporeal Protein A perfusion system. There is no prior report in the literature or elsewhere of antitumor effects ascribable to this group of proteins.

Enterotoxins have distinct advantages in inducing tumor killing effects over the more cumbersome and elaborate Staphylococcal Protein A plasma perfusion systems. One advantage is that enterotoxins are relatively simple proteins that may be infused after being solubilized in saline. This solubility obviates the need to immobilize Protein A or other biologicals on a solid support, and eliminates the requirement for perfusing plasma over a solid surface. Moreover, it bypasses problems associated with potential toxic reactions to impurities of Protein A. Consequently, enterotoxins appear to be far safer and more effective than previously described systems. Moreover, the system requires no elaborate sterilization and there is no problem with potential leaching of immobilized materials or chemical products from an inert surface as there would be with an extracorporeal column. Hence, this product offers decided advantages of effectiveness and convenience over the original system. Indeed, all evidence points to enterotoxins as being the most active antitumor product in the Staphylococcal Protein A plasma perfusion system.

SUMMARY OF THE INVENTION

The present invention provides enterotoxins derived from *Staphylococcus aureus* and superantigens which are useful by themselves for the treatment of cancer. Enterotoxins are known to have molecular weights ranging from 22,000 to 38,000. They are heat stable, and resistant to trypsin digestion. According to one aspect of the present invention, enterotoxins isolated from media which is supporting the growth of various *Staphylococcus aureus* organisms are used in relatively pure form. When administered to subjects having tumors, the preparation induces a tumoricidal reaction resulting in tumor regression. It should be understood that the term, "tumoricidal reaction," as used herein, means that the material under discussion promotes or assists in the killing of tumor cells.

Chemical derivatization of the native enterotoxin molecule in order to minimize toxicity results in a preparation that also induces tumoricidal reactions and tumor regression when administered to tumor bearing hosts.

Streptococcal pyrogenic exotoxin A, which has been shown to have statistically significant structural homology to enterotoxin B, is also useful for the treatment of cancer.

Synthetic polypeptides with substantial structural homology and with statistically significant sequence homology and similarity to Staphylococcal enterotoxins and Streptococcal pyrogenic exotoxins, including alignment of cysteine residues and similar hydropathy profiles, are also described as effective in tumoricidal therapy. In addition to enterotoxins, such peptides might be derived from but not limited to sequences in additional superantigens such as minor lymphocyte stimulating loci, mycoplasma and mycobacterial antigens, heat shock proteins, stress peptides, and mammary tumor viruses.

Enterotoxin gene transfection of tumor cells, accessory cells or immunocytes resulting in surface expression of enterotoxins with augmented immunogenicity is also described as useful in this application.

Genetically engineered enterotoxins or peptides using recombinant DNA technology are also described as useful as tumoricidal therapy. Enterotoxin peptides and homologous amino acid sequences to block or destroy autoreactive T and B lymphocyte populations in autoimmune diseases are also described in this application.

DESCRIPTION OF THE SPECIFIC EMBODIMENTS

The enterotoxins of *Staphylococcus aureus* form a group of serologically distinct extracellular proteins, designated A, B, $C_1$, $C_2$, $C_3$, D, E and F. These proteins are recognized as the causative agents of Staphylococal food poisoning. Enterotoxin F appears to be important in the pathogenesis of the Staphylococcal toxic shock syndrome. Ingestion of preformed entetotoxin in contaminated food leads to the rapid development (within two to six hours) of symptoms of vomiting and diarrhea that are characteristic of Staphylococcal food poisoning.

The enterotoxin proteins are of similar molecular weight. Characteristically, they have a disulfide loop near the middle of the molecule, and are easily soluble in water and salt solutions. They are relatively resistant to proteolytic enzymes and to heat. The higher level structural similarities between the enterotoxins is in agreement with the clinical picture where all of the enterotoxins seem to produce similar effects of sepsis, hypotension and fever. General properties of the enterotoxins are given in Table 1.

TABLE 1A

SOME PROPERTIES OF THE ENTEROTOXINS

| | Enterotoxin | | | |
|---|---|---|---|---|
| | A[a] | B[b] | $C_1$[c] | $C_2$[d] |
| Emetic dose ($ED_{50}$)($\mu$g/monkey) | 5 | 5 | 5 | 5–10 |
| Nitrogen content (%) | 16.5 | 16.1 | 16.2 | 16.0 |
| Sedimentation coefficient ($S_{20,w}$)(S) | 3.04 | 2.78 | 3.00 | 2.90 |
| Diffusion coefficient ($D_{20,w}$)($\times 10^{-7}cm^2sec^{-1}$) | 7.94 | 8.22 | 8.10 | 8.10 |
| Reduced viscosity (ml/gm) | 4.07 | 3.81 | 3.4 | 3.7 |
| Molecular weight | 34,700 | 30,000 | 34,100 | 34,000 |
| Partial specific volume | 0.726 | 0.726 | 0.728 | 0.725 |
| Isoelectric point | 6.8 | 8.6 | 8.6 | 7.0 |
| Maximum absorption (m$\alpha$) | 277 | 277 | 277 | 277 |
| Extinction ($E_{1\ cm}^{1\%}$) | 14.3 | 14.4 | 12.1 | 12.1 |

[a]F. S., Thadhani, K., Schantz, E. J., Bergdoll, M. S., Biochemistry 5, 3281, 1966.
[b]Bergdoll, M. S., Borja, C. R., Avena, R. M., J. Bacteriol. 90, 1481, 1965.
[c]Borja, C. R., Bergdoll, M. S., Biochemistry 6, 1467, 1967.
[d]Avena, R. M., Bergdoll, M. S., Biochemistry 6, 1474, 1967.

TABLE 1B

Physicochemical Properties of Staphylococcal Enterotoxins*

| | Enterotoxin | | | | | |
|---|---|---|---|---|---|---|
| Property | A[a] | B[b] | $C_1$[c] | $C_2$[d] | D[e] | E[f] |
| Emetic dose for monkey ($\mu$g) | 5 | 5 | 5 | 5–10 | — | — |
| Sedimentation coefficient ($S_{20,w}$) | 3.03 | 2.89 | 3.0 | 2.9 | — | 2.6 |
| Molecular weight | 27,800 | 28,366[g] | 26,000 | 34,100 | 27,300 | 29,600 |
| Isoelectric point | 7.26 | 8.6 | 8.6 | 7.0 | 7.4 | 7.0 |
| C-terminal residue | Serine | Lysine | Glycine | Glycine | Lysine | Threonine |
| N-terminal residue | Alanine | Glutamic acid | Glutamic acid | Glutamic acid | Serine | — |

[a]Schantz, E. J., Roessler, W. G., Woodburn, M. J., Lynch, J. M., Jacoby, H. M., Silverman, S. J., Gorman, S. J., Biochemistry 11, 360, 1972.
[b]Schantz, E. J., Roessler, W. G., Wagman, J., Spero, L., Dunnery, D. A., Bergdoll, M. S., Biochemistry 4, 1011, 1965.
[c]Borja, C. R., Bergdoll, M. S., Biochemistry 6, 1467 (1967).
[d]Avena, R. M., Bergdoll, M. S. Biochemistry 6, 1474 (1967).
[e]Chang, P. C., Bergdoll, M. S., Biochemistry, 18, 1937, 1979.
[f]Borja, C. R., Fanning, E., Huang, I. Y., Bergdoll, M. S., J. Biol. Chem. 247, 2456, 1972.
[g]Dayhoff, M. ed. (1972) Data Section. In Atlas Protein Sequence Structure 5 : D227 National Biomedical Research Foundation, Washington, D. C. (determined from the amino acid sequence of Huang and Bergdoll, 1970). Huang, I. Y., Bergdoll, M. S., J. Biol. Chem. 245, 3493, 1970.
*Modified from Bergdoll, M. S., Czop, J. K., Gould, S. S., Enterotoxin Synthesis by the Staphylococci. In: Recent Advances in Staphylococcal Research, pp. 307–316, Yotis; W. W. (Ed.) Ann. N. Y. Acad. Sci. Vol. 236.

Amino acid compositions of enterotoxins A, B, $C_1$, $C_2$ and E reveal a high content of lysine, aspartic acid and tyrosine. Enterotoxins A and E are similar in methionine, leucine and arginine content, differing in this regard from enterotoxins B, $C_1$ and $C_2$. The amino acid sequence of enterotoxin B was found to consist of 239 amino acids. Half-cystine residues found at positions 92 and 112 form a disulfide bridge, and it has been suggested that the primary structure in this region may be common to all of the enterotoxins.

The protein sequences and immunological cross reactivity of the enterotoxins reveal that they can be divided into two related groups, SEA (Staphylococcal enterotoxin A), SEE and SED constitute one group, and SEB, SEC and Streptococcal pyrogenic exotoxin A (SPEA) make up the second group. Amino acid sequences show that SEA and SEE are almost identical and that SEB, SEC and SPEA share regions of similar sequence. SED is moderately related to both groups although it is more similar to the SEA group. There is a striking amino acid similarity among enterotoxins A, B, C, D and E in the region immediately downstream from cystine located at residue 106 in SEA. A second region at residue 147 also shows a highly conserved sequence. These regions are contained on the peptide fragment of SEC, shown to contain the active sites for emesis and diarrhea. The mitogenic region resides in the C terminal tryptic fragment of SEC, implying that other regions of sequence similarity exist. Amino acid sequence similarities and congruences are given in Tables 2–4.

TABLE 2*

SEQUENCE SIMILARITIES AMONG THE PYROGENIC TOXINS AND ENTEROTOXINS

| TOXIN | SEQUENCE | |
|---|---|---|
| | 106____________119 | 147______________163 |
| SEA | CMYGGVTLHDNNRL | KKNVTVQELDLQARRYL |
| SEB | CMYGGVTEHHGNOL | KKKVTAQELDYLTRHYL |
| SEC1 | CMYGGITKHEGNHF | KKSVTAQELDIKARNFL |
| SED | CTYFFVTPHEGNKL | KKNVTVQELDAQARRYL |
| SEE | CMYGGVTLHDNNRL | KKEVTVQELDLQARHYL |
| Con-sensus | CMYGGVTLHEGNHL | L R<br>KKKNVTAQELD-QAR-YL<br>Y H |
| TSST-1 | IHFQISGVTNTEKL | KKQLAISTLDFEIRHQL |

*Iandolo, J. J., Annu. Rev. Microbiol., 43, 375, 1989.

TABLE 3

Amino Acid Composition of the Enterotoxins (g 100 g protein)

| Amino Acid | Enterotoxin A* | B† | $C_1$‡ | $C_2$‡ | E§ |
|---|---|---|---|---|---|
| Lysine | 11.26 | 14.85 | 14.43 | 13.99 | 10.83 |
| Histidine | 3.16 | 2.34 | 2.91 | 2.87 | 3.04 |
| Arginine | 4.02 | 2.69 | 1.71 | 1.75 | 4.50 |
| Aspartic acid | 15.53 | 18.13 | 17.85 | 18.38 | 15.10 |
| Threonine | 5.96 | 4.50 | 5.31 | 5.80 | 6.36 |
| Serine | 2.99 | 4.05 | 4.58 | 4.81 | 4.72 |
| Glutamic acid | 12.36 | 9.45 | 8.95 | 8.93 | 12.15 |
| Proline | 1.35 | 2.11 | 2.16 | 2.23 | 1.93 |
| Glycine | 2.96 | 1.78 | 2.99 | 2.90 | 4.10 |
| Alanine | 1.94 | 1.32 | 1.85 | 1.61 | 2.38 |
| Half-cystine | 0.66 | 0.68 | 0.79 | 0.74 | 0.81 |
| Valine | 4.93 | 5.66 | 6.50 | 5.87 | 4.36 |
| Methionine | 0.96 | 3.52 | 3.20 | 3.60 | 0.45 |
| Isoleucine | 4.11 | 3.53 | 4.09 | 4.02 | 4.30 |
| Leucine | 9.78 | 6.86 | 6.54 | 6.13 | 10.08 |
| Tyrosine | 10.63 | 11.50 | 9.80 | 10.27 | 9.79 |
| Phenylalanine | 4.31 | 6.23 | 5.35 | 5.25 | 4.47 |
| Trytpophane | 1.46 | 0.95 | 0.99 | 0.84 | 1.51 |
| Amide $NH_3$ | 1.80 | 1.66 | 1.71 | 1.62 | 1.66 |
| TOTAL | 98.37 | 100.15 | 100.00 | 99.99 | 100.88 |

*Schantz et al., 1972.
†Bergdoll, M. S., Chu, F. S., Huang, I. Y., Rowe, C., Shih, T., Arch Biochem Biophys, 112, 104, 1965.
‡Huang, I. Y., Shih, T., Borja, C. R., Avena, R. M., Bergdoll, M. S., Biochemistry, 6, 1480, 1967.
§Borja et al., 1972.
¶From Bergdoll, M. S., Huang, I. Y., Schantz, E. J., J. Agric. Food Chem. 22, 9, 1974.

TABLE 4†

Amino Acid Compositions of TSST-1a and 1b[a]

| Amino acid | Amino acid composition: TSST-1a residues per mole[b] | TSST-1b residues per mole[b] | TSST-1 clone[b] |
|---|---|---|---|
| Aspartic acid | 26 | 27 | 25 |
| Threonine | 21 | 20 | 19 |
| Serine | 20 | 20 | 21 |
| Glutamic acid | 20 | 20 | 17 |
| Proline | 10 | 8 | 10 |
| Glycine | 13 | 14 | 11 |
| Alanine | 4 | 5 | 3 |
| Half-cystine | 0 | 0 | 0 |
| Valine | 5 | 5 | 5 |
| Methionine | 0 | 0 | 2 |
| Isoleucine | 15 | 15 | 17 |
| Leucine | 14 | 16 | 15 |
| Tyrosine | 10 | 8 | 9 |
| Phenylalanine | 7 | 7 | 7 |
| Histidine | 5 | 5 | 5 |
| Lysine | 23 | 24 | 21 |
| Tryptophan | ND[d] | ND[d] | 3 |
| Arginine | 4 | 5 | 4 |
| | 197 | 199 | 194 |

†Blomster-Hautamaa, D. A., Schlievert, P. M., Methods in Enzymology, 165, 37, 1988.
[a]Isolated from strain MN8, as compared to the inferred amino acid composition of the TSST-1 structural gene.
[b]Residues per mole values are based on a molecular weight of 22,000.
[c]Residues per mole inferred from the DNA sequence of the TSST-1 structural gene. Blomster-Hautamaa and colleagues.
[d]ND. Not determined.

Comparison of the primary sequences of the staphylococcal enterotoxins and their relatives is shown in Table 20. The complete primary amino acid sequences of the staphylococcal enterotoxins and related proteins are shown aligned, with the exception of the sequences of the exfoliating toxins, which are shown aligned with each other, but not with the remaining toxins. The exfoliating toxin sequences are shown here for completeness, and because these toxins have properties related to those of the others (see below). Toxins shown are as follows: SEA to SEE, *Staphylococcus aureus* enterotoxins A to E; SPE A and C, *Streptococcus pyogenes* toxins A and C; TSST1, *Staphylococcus aureus* toxic shock—associated toxin; ETA and ETB, *Staphylococcus aureus* exfoliating toxins A and B. Data are from (9–17). Residues that are identical or that have changed to an amino acid with similar properties among at least two of the following: SEA, SEE, and SED, are highlighted in pink. Residues that are identical or that have changed to an amino acid with similar properties among at least two of the following: SEB, SEC1, and SED and at least two of SEB, SEC1, and SEC2, are highlighted in yellow. Single letter abbreviations for the amino acid residues are: A, Ala; C, Cys; D, Asp; E, Glu; F, Phe; G, Gly; H, His; I Ile; K, Lys; L, Leu; M, Met; N, Asn; P, Pro; Q, Gln; R, Arg; S, Ser; T, Thr; V, Val; W, Trp; and Y, Tyr.

There is evidence that indicates varying degrees of immunological relatedness between certain enterotoxins, Bergdoll, M. S., Borja, C. R., Robbins, R., Weiss, K. F., Infect. Immun., 4, 593, 1971; Bergdoll, M. S., Enterotoxins. In; Staphylococci and Staphylococci Infections ed. C. S. F. Easmon, C. Adlam 1, pp. 559–598, 1983, Landon, Academic; Freer, J. H., Arbuthnott, J. P., Pharm. Ther., 19, 55, 1983. A considerable degree of cross reactivity exists for antisera raised against one enterotoxin and other enterotoxins. It has been considered that the enterotoxins may contain major cross reactive antigenic sites, while each individual enterotoxin possesses minor specific antigenic regions. Common precipitating antibodies were formed between SEA and SED. In addition, enterotoxins B and C can react immunologically with antisera against either toxin type. Immunologic cross reactivity between Streptococcal pyrogenic. exotoxin A and Staphylococcal enterotoxins B and $C_1$ has been shown. These results suggest a conserved domain present in the three exotoxins. SEA, SEB, SEC, ED, TSS-1 and the pyrogenic exotoxins have also been shown to share considerable DNA and amino acid homology. The enterotoxins, the pyrogenic exotoxins and TSST-1 therefore a to be evolutionarily related and all belong to a common generic group of proteins.

It should be noted that the two Streptococcal toxins SPEA and C are about as similar to each of the Staphylococcal groups as they are to each other. Exfoliative toxins are of similar size to SEB and SEA with similar modes of action. They share several points of sequence similarity to the Staphylococcal enterotoxins. Overall there are several stretches at which similarities are apparent throughout the total group comprised of Staphylococcal enterotoxins, Streptococcal pyrogenic exotoxins and staphylococcal exfoliative toxins. The longest of these, located two-thirds of the way through the proteins, is similar to sequences found at the COOH-terminal end of the human and mouse invariant chain.

Invariant chain is a polypeptide associated with nascent MHC class II molecules. Class II molecules bind peptides and present them to T cells during immune responses. Indeed, many toxins bind to class II molecules. The shared sequences may indicate some or all of the invariant chain and toxin binding sites on class II molecules.

The known structural homology between the enterotoxins and Streptococcal pyrogenic exotoxin is further supported by the identity of clinical responses. It is known that this exotoxin induces hypotension, fever, chills and septic shock in man. It is hypothesized that this compound activates cytokines, such as interleukin 1, interleukin 2, tumor necrosis factor and interferon, and procoagulant activity which are the prime mediators of the clinical symptomatology. It is hypothesized that many other bacterial products are capable of inducing similar in vivo activity. Among potential tumoricidal agents which are likely candidates based upon structural homology or identity of clinical symptomatology are gram positive bacterial products, cell wall bacterial constituents such as peptidoglycans and various gram negative bacterial components to include meningococcal, pseudomonous and *E. coli* products. While presently undemonstrated in animal systems, it is believed that these agents are likely to possess similar tumoricidal utility as those claimed here for the enterotoxins.

The recognition that the biologically active regions of the enterotoxins and SPEA were substantially,structurally homologous enables one to predict synthetic polypeptide compounds which will exhibit similar tumoricidal effects. FIG. 2 illustrates the amino acid sequence homology of mature SPEA and *Staphylococcus aureus* enterotoxin B. The top sequence is the SPEA-derived amino acid sequence. The amino acid sequence of enterotoxin B is on the bottom. Sequences are numbered from the amino acid terminus, with amino acids represented by standard one character designations. (See Tables 5 and 6 below.) Identities are indicated by: and gaps in the sequences introduced by the alignment algorithm are represented by dashed-lines. See Johnson, L. P., L'Italien, J. J., and Schlievert, P. M.,. "Streptococcal pyrogenic exotoxin type A (scarlet fever toxins) is related to *staphylococcus aureus* enterotoxin B," Mol. Gen. Genet. (1986) 203: 354–356.

One common methodology for evaluating sequence homology, and more importantly statistically significant similarities, is to use a Monte Carlo analysis using an algorithm written by Lipman and Pearson to obtain a Z value. According to this analysis, a Z value greater than 6 indicates probable significance, and a Z value greater than 10 is considered to be statistically significant. Pearson, W. R., Lipman, D. J., "Improved tools for biological sequence comparison," *Proc. Natl. Acad. Sci. USA*, April 1988, 85 (8) pages 2444–8; Lipman, D. J., Pearson, W. R., "Rapid and sensitive protein similarity searches," *Science*, Mar. 22, 1985, 227 (4693) pages 1435–41.

In the present invention, synthetic polypeptides useful in tumoricidal therapy and in blocking or destroying autoreactive T and B lymphocyte populations are characterized by substantial structural homology to enterotoxin A, enterotoxin B and streptococcal pyrogenic exotoxins with statistically significant sequence homology and similarity (Z value of Lipman and Pearson algorithm in Monte Carlo analysis exceeding 6) to include alignment of cysteine residues and similar hydropathy profiles.

TABLE 5

| Amino Acid | One-letter Symbol |
|---|---|
| Alanine | A |
| Arginine | R |
| Asparagine | N |
| Aspartic acid | D |
| Cysteine | C |
| Glutamine | Q |
| Glutamic acid | E |
| Glycine | G |
| Histidine | H |
| Isoleucine | I |
| Leucine | L |
| Lysine | K |
| Methionine | M |
| Phenylalanine | F |
| Proline | P |
| Serine | S |
| Threonine | T |
| Tryptophan | W |
| Tyrosine | Y |
| Valine | V |

TABLE 6

```
           10        20             30        40        50
 STR-PKPSQLQRSNLVKTFKIYIFFMRVTL-----VTHENVKSVDQLLSHDLIYNVS--
 :   :::  :  :   : :      : : :     :   ::::       ::::  :
ESQPDPKPDELHKSS--K-FTGLMENMKV-LYNNDHVSAINVKSINEFF--DLIYLYSIK
         10           20        30         40          50
```

TABLE 6-continued

```
            60        70        80       90
----GPNYDKLKTELKNQEMATLFKDKNVDIYGVEYYHLCYLC---------ENAERSAC
    : :::    : ::   :   ::: ::  :  ::  ::          ::   :  :
DTKLG-NYDNVRVEFKNKDLADKYKDKYVDVFGANYYQ-CYFSKKTNNIDSHENTKRKTC
      60        70        80        90         100       110

 100       110            120       130       140        150
LYGGVTNHEGNHLEIPKK----IVVKVSIDGIQSLSFDIEQIKNGNCSRIS-YTVRKYLT
 ::::: :  : :    :    : : :  ::   ::::    :         :  : ::
MYGGVTEHGNNQLD---KYYRSITVRVFEDGKNLLSFDVQTNKKKVTAEQLDYLTRHYLV
       120          130       140       150       160

      160       170       180       190         200
DNKQLYTNGPSKYETGYIKFIPKNKESFWFDFFPEPE--FTQSKYLMIYKDNETLDSNTS
 :: ::    : :::::::::  :  ::: :  : :   : :::::: :      ::
KNKKLYEFNNSPYETGYIKFIE-NENSFWYDMMPAPGNKFDQSKYLMMYNNDKMVDSKDV
170       180       190        200       210       220

        220
QIEVYLTTK
 ::::::::
KIEVYLTTKKK
 230
```

The enterotoxins are presumed to function by affecting emetic receptors in the abdominal viscera which stimulate the emetic and diarrheal response. These toxin also stimulate T lymphocyte mitogenicity, procoagulant, chemotactic activity, as well as cysteinyl leukotriene, lymphokine, serine protease and thromboglobulin production. Cytokines knowm to be induced by enterotoxins induce interferon, tumor necrosis factor, interleukins 1 and 2. They suppress immune responses, augment natural killer cell cytotoxicity, enhance gram-negative endotoxic lethality and induce fever and hypotension. These additional properties are shared with the pyrogenic exotoxins of both *Staphylococcus aureus* and *streptococcus pyogenes* and TSST-1. Synthetic polypeptides would also be expected to demonstrate similar responses.

The Staphylococcal enterotoxins A, B, C, D, E, toxic shock toxin (TSST-1), a product of mycoplasma arthritidis, mycobacterial species, heat shock peptides and Mls antigens provoke dramatic T cell responses. Staphylococcal enterotoxins are the most powerful T cell mitogens known eliciting strong polyclonal proliferation at concentrations $10^3$ lower than such conventional T cell mitogens as phytohemagglutinin. SEA is the most potent T cell mitogen, stimulating DNA synthesis at concentrations of $10^{-13}$ to $10^{-16}$ M in the human system. All stimulate a large proportion of both murine and human CD4+ and CD8+ T cells. Activity of these mitogens is tightly restricted by the major histocompatibility complex (MHC) class II antigens. It is proposed that the staphylococcal enterotoxins, streptococcal pyrogenic exotoxins, exfoliative toxins and a product of mycoplasmm arthritidis bind directly to the T cell receptor and to class II MHC. These two structures are brought into contact, thus stimulating T cell activation via the $V_\beta$ region of the T cell receptor mimiking strong alloreactive response.

Many toxins have binding affinities for MHC class II molecules which are involved in stimulating T cells. For example, SEA has a Kd for human class II about $3.2\times10^{-7}$ M, SEB of $10^{-6}$ M and TSST-1 of $10^{-7}$ M. SEA and SEB probably bind t the same site on class II because they cross compete for binding. Exfoliative toxins bind only weakly or not at all to class II. SEB and TSST-1 have different binding sites on class II molecules.

The structure of class II consists of two immunoglobulin-like domains located close to the cell membrane which supports a structure Constructed from the $NH_2$ terminal regions of both polypeptides of the protein and comprise an extended β-pleated sheet supporting two alpha helices separated by a cleft. Peptides derived from foreign materials or from proteolysis of self proteins normally lie in this groove. It is this complex of MHC and peptide that stimulates T cells bearing alpha and beta receptors. Bacterial toxins do not normally bind to MHC molecules by occupying this groove and therefore do not behave like conventional peptide-MHC binding antigens. Toxins bind to three different class II proteins, namely DR, DP, DQ (or murine I-A, I-E). SEB and TSST-1 bind to DR and DQ alleles but not to DP. Toxin-class II complexes stimulate T cells. Most toxins bind preferentially to DR class II proteins, less well to DQ and not at all to DP. Different DR alleles have different affinities for a few of the toxins most notably SEE. In the souse, complexes of toxins plus I-E (murine DR equivalent) stimulate T calls more efficiently than complexes of toxins with I-A (murine DQ analog). There is also evidence for weak. haplotype specificity, e.g., toxins bound to I-$A^k$ stimulate T cells less well than toxins bound to I-$A^d$ or I-$A^b$. *Staphylococcus aureus* toxins bind more efficiently to human class II proteins than to mouse. A likely location for toxin binding to MHC may be at the sides of class II where 2 wings, the ends of the β-pleated strands, extend to either side of the proteins.

A hypothetical structure for the complex of class II MHC T cell receptor and Staphylococcal enterotoxins and MHC protein is given in FIG. 1, page 761 of Herman, A. *et al., Ann. Rev. Immunol.* 9:745–772 (1991). The Figure shows a class II MHC protein, diagrammed according to Bjorkman and co-workers and Brown and co-workers, in contact with a T cell receptor and a staphylococcal enterotoxin or Mls product. Ag is the probable site of binding of a conventional antigenic peptide.

Toxins stimulate T cells through $V_\beta$ binding. T cell receptors for antigenic peptides bound to MHC proteins are made up of 5 clonally variable components $V_\alpha$, $J_\alpha$, $V_\beta$, $D_\beta$, and $J_\beta$. Recognition of most conventional antigenic peptides bound to MHC proteins involve contributions from all the variable components of the T cell receptor.

In contrast, the toxins stimulate T cells almost exclusively via the $V_\beta$ region of the T cell receptor. See Table 7 for binding of toxins to T cells bearing various $V_B$ receptors.

TABLE 7

| | $V_\beta$ SPECIFICITY | |
|---|---|---|
| TOXIN | HUMAN | MOUSE |
| SEA | ? | 1, 3, 10, 11, 17 |
| SEE | 5.1, 6.1–3, 8, 18 | 11, 15, 17 |
| SED | 5, 12, ? | 3, 7, 8.1–3, 11, 17 |
| SEB | 3, 12, 14, 15, 17, 20 | 3, 7, 8.1–3, 17 |
| SEC1 | 12, ? | 3, 8.2, 8.3, 11, 17 |
| SEC2 | 12, 13.1, 13.2, 14, 15, 17, 20 | 3, 8.2, 10, 17 |
| SEC3 | 5, 12, ? | 3, 7, 8.1, 8.2 |
| TSST1 | 2 | 3, 15, 17 |
| ExFT | 2 | 3, 10, 11, 15, 17 |
| MAM | ? | 6, 8.1, 8.2, 8.3 |

This property of selective stimulation of $V_\beta$ is reminiscent of the endogenous superantigens called Mls antigens in the mouse. The pattern of $V_\beta$ specificity of the different toxins corresponds loosely with their groupings by sequence similarity. SEA, SED and SEE all stimulate murine T cells bearing $V_\beta 11$ and SEE and SED both stimulate human T cells bearing $V_\beta 5$. SEB and SECs stimulate mouse T cells bearing members of the $V^\beta 8$ family and human T cells positive for $V_\beta 12$. The exceptions are as follows: SED stimulates T cells bearing the $V_\beta 8$ unlike SEA and SEE. Exfoliating toxin and TSST-1 which are not related by sequence have similar specificities for $V_\beta$ both in mouse and humans.

Bacterial toxins and other superantigens do not bind to T cell receptors at those regions involved in binding to conventional antigenic peptides plus MHC. The superantigens engage $V_\beta$ on an exposed face of $V_\beta$ or a region predicted to be a β-pleated sheet and exposed on the side of the T cell receptor. This model predicts that toxins act as clamps engaging the sides of class II and $V_\beta$ bringing into close proximity the surfaces of the T cell receptor and MHC that would contact each other during T cell recognition of conventional antigens bound in the groove of NBC. Proper confirmation must await x ray crystallographic resolution of the complex.

Neither class II nor toxins separately have affinities for the T cell receptors in question, but the combination of toxin and class II proteins do. Only if the complex peptide-MHC ligand has formed can it functionally engage the T cell receptor. The T cell activation via the $V_\beta B$ region of the T cell mimics strong alloreactive responses. This interaction occurs irrespective of whether the Vβ is expressed on CD4+ or CD8+ T cells. This behavior is consistent with the known resistance of Staphylococcal enterotoxins to proteolysis even in acidified conditions.

Mice Express Endogenous Equivalent of the Enterotoxins

T cells from some mice responded well to spleen cells from some other animals even though both responder and stimulator were identical at the MHC. The antigens are called minor lymphocyte stimulating antigens (Mls). There are many Mls-like products produced by mice controlled by non-linked loci. Mls products stimulate T cells bearing $V_\beta$s. Mls-$1^a$ in combination with mouse class II molecules stimulate nearly all T cells bearing mouse $V_\beta$ 6, 7, 8.1 and 9. A list of the Mls-like products and the $V_\beta$s they engage is given in Table 8. Mls products have not yet been found in humans.

TABLE 8

Mls-like products identified in mouse.

| LOCUS | $V_\beta$ specificity | MHC association |
|---|---|---|
| Mls-$1^a$ | 6, 7, 8.1, 9 | Class II (except q) |
| Mls-$2^a$ | 3 | Class II (except q) |
| Mls-$3^a$ | 3 | Class II (except q) |
| ? | 5 | I-E |
| ? | 7 | I-E |
| ? | 11 | I-E |
| ? | 17 | I-E |

A striking resemblance exists between T Cell responses to Staphylococcal enterotoxins and T cell responses to the Mls locus. The Mls locus located on chromosome 1 and other similar genes on other (unknown) chromosomes have profound effect on T cells. Polymorphism at these loci elicits a strong primary mixed lymphocyte response between MHC identical and Mls disparate spleen cells in mice.

Mls products stimulate T cells bearing particular $V_\beta 5$ almost regardless of the rest of the structure of the receptor on the T cell. This activity depends on the simultaneous expression by the presenting cell of class II proteins. Some class II products, most notably I-E molecules, present Mls products and bacterial toxins better than others. Mls appear to engage $V_\beta$s at the same site on the exposed face of the polypeptide as toxins.

The similarities between properties of bacterial toxins and mouse Mls products might lead one to suggest a structural similarity. Mls products associate with class II and stimulate T cells via $V_\beta$ much like superantigens but the structure of Mls is unknown.

There are consequences for mice expressing Mls products. They cause deletion in the thymus for all prospective T cells bearing $V_\beta$S with which they interact. Mice expressing Mls-$1^a$ contain very few T cells bearing $V_\beta 6$, 7, 8.2 or 9 and hence are deprived of 20% of their, total potential T cell repertoire. Despite this they do not seem to be susceptible to disease.

Both Mls and enterotoxins show the following characteristics in common:

1. Both activate a high frequency of normal T cells exceeding that of conventional protein antigens.
2. Responding T cells are $CD4^+$.
3. T cells of many specificities respond.
4. Both elicit responses of T cells expressing receptors having particular $V_\beta$ gene products.
5. There is no MHC restriction of responding T cells.
6. Both require presentation by class II MHC.
7. IE and IA molecules on antigen presenting cells are required for immunologic effects.
8. Ontogenetic deletion of $V_\beta$ or $CD4^+8^+$ cells is induced by both molecules.

These similarities are summarized in Table 9.

TABLE 9

Similarities between the T cell responses to Mls and SE and differences with responses to protein Ag[a]

| Characteristic of the T Cell Response to: | Mls-1[a] | SE | Proteins |
|---|---|---|---|
| High frequency of responding cells | Yes(~1:5) | Yes(~1:5) | No(~1:$10^4$) |
| Responding T cells $CD4^+$ | Yes | Yes | Yes[b] |
| T cell receptor involved in response | Yes | Yes | Yes |
| T cells of many specificities respond | Yes | Yes | No |
| $V_\beta$ restriction of responding T cells | Yes | Yes | No[c] |
| MHC restriction of responding T cells | No | No | Yes |
| Incompetent class II MHC alleles | Yes | Yes | Yes[d] |
| 1-E more involved than 1-A | Yes | Yes | No |
| Ontogenetic deletion of $V_\beta$ on $CD4^+8^+$ | Yes | Yes[e] | No |
| Processing required | ? | No | Yes |
| Pulsing APC stimulatory | ? | Yes | Yes |
| Pulsing T cell stimulatory | ? | Yes | No |
| Protein identified | No | Yes | Yes |

[a]Data on T cell responses to Mls and SE derived from this paper and Janeway et al. A detailed description of the SE themselves is found in Bergdoll.
[b]T cells expressing CD8 respond only to proteins degraded within cells; extrinsic proteins are presented by class II MHC to CD4 T cells.
[c]T cell responses to protein antigens require all elements of the TCR, whereas those to Mls and SE appear to require only use of certain $V_\beta$ segments.
[d]Presentation of proteins is much more restricted in use of allelic forms of class II MHC molecules than is "presentation" of SE or Mls.
[e]From Yagi and Janeway.

The striking functional similarity of Staphylococcal enterotoxins and Mls suggests that the Mls may represent a protein with homology to Staphylococcal enterotoxins. It has been proposed that the Mls like Staphylococcal enterotoxins directly binds the TCR-CD4 complex via its $V_\beta$ domain and to class II MHC molecules assembling a complex that is highly stimulatory for T Cells. Hence, both Mls and staphylococcal enterotoxins are thought to ligate class II MHC to the TCR:CD4 complex in such a way as to stimulate a large percentage of T cells with restricted $V_\beta$ usage.

While the animal studies described herein were carried out with Staphylococcal enterotoxins A, B, C, D, E TSST-1 and Streptococcal pyrogenic exotoxins, based upon the observed structural and reactive similarities, it would be expected that similar results would be obtained with the other superantigens such as mycoplasma and mycobacterial antigens, Mls antigens, heat shock proteins and the synthetic polypeptides described above. Additional biological properties common to this group include their mitogenic effects, interferon, interleukin and tumor necrosis factor induction activity. Furthermore, all are capable of inducing fever and shock when given intravenously to rabbits or monkeys, and most of these have been implicated as potential pathogenic agents in the toxic shock syndrome.

Production and Isolation of Enterotoxins A, B, C, D, E and F

General Methods

Isolation and purification procedures for enterotoxins contain numerous common steps. On the whole, growth of enterotoxin producing *Staphylococcus aureus* strains is similar in all oases. The most widely used general medium for the culture of these organisms contains 3% MZ-amine Type A, or MAX, 3% protein hydrolysate powder, 0.00005% thiamine and 0.001% niacin. Optimum yields of the enterotoxins are obtained under controlled fermentation, where pH, temperature and oxygen tension are controlled. Typically, growth at 37° C. for 18 to 24 hours is sufficient for maximum toxin yields. The yield of enterotoxin B and $C_1$ and $C_2$ will be up to several hundred $\mu$grams (toxin)/ml (media), while the yield of other toxins will be only a few $\mu$grams/ml.

All enterotoxins are secreted products. Generally, they are produced during the logarithmic and stationary stages of cell growths. After growth, the producing cells are removed from the medium by centrifugation, and the toxin-containing supernatant is saved. If a large fermentation has been carried out, then the cells and supernatant can be quickly separated using a continuous flow centrifuge. To concentrate the toxins from the media, various methods, e.g., polyethylene glycol precipitation, or dialysis tubing precipitation, or hollow fiber concentration using membranes with selective molecular weight cutoffs can be used. To assess the purity of the isolated enterotoxin product, specific antisera to each of the toxins are used in appropriate quantitative immunoassays, e.g., radioimmunoassays or enzyme labelled immunoassays, hemagglutination, or precipitin reactions.

Enterotoxin Purification by Type

Enterotoxin B

The strain of *Staphylococcus aureus*, that is used for the production of SEB (Staphylococal enterotoxin B) is e.g., S6 or 10–275. (source: Dr. John Iandolo, Kansas State University, Manhattan, Kans.) The medium containing the toxin is diluted twice with water adjusted to a pH of 6.4, and AmberLite CG-50 (200 mesh) cation ion-exchange resin is added to the toxin mixture. The toxin is eluted, dialyzed, then reapplied to the CG-50 column again. The eluted toxin is dialyzed then applied to a column of carboxymethyl cellulose or CM-sephadex. Unbound proteins are eluted with 0.03 and 0.04 molar sodium phosphate buffer. At this point, the toxin is essentially homogeneous. Using chromatofocusing techniques, the SEB may be further subdivided into several isoelectric species using polybuffer 96.

Enterotoxin A (SEA)

High SEA producers, e.g., *Staphylococcus aureus* 13M-2909 (Source: Dr. John Iandolo, Kansas State University, Manhattan, Kans.) are grown in the general medium that is made 0.2% in glucose. Initially, AmberLite CG-50 is used for batch, isolation. After incubation, the toxin is eluted and dialyzed. The toxin is then loaded onto a CM-cellulose column and eluted with a linear gradient. The combined fractions are then loaded onto a hydroxylapatite column and eluted using a linear gradient. The fractions are lyophilized and chromatographed on a Sephadex-G-75 column. The toxins obtained from this procedure are greater than 99% pure, with a yield of approximately 20%.

Enterotoxin $C_1$ ($SEC_1$)

Culture supernatant from *Staphylococcus aureus* 137 (Source: Dr. Marcia Betley, University of Wisconsin, Madison, Wis.) is concentrated, dialyzed and lyophilized. The toxin product is then applied to a carboxyuethyl cellulose column and eluted with a stepwise gradient. The toxin peak consists of a sharp peak with a trailing edge. The eluted toxin is concentrated and applied to Sephadex-G-75. The toxin elutes as a single peak. The toxin is then concentrated and run twice through a column of Sephadex-G-50. The eluate is dialyzed against water and lyophilized.

Enterotoxin $C_2$ ($SEC_2$)

Culture supernatant from *Staphylococcus aureus* 361 (Source: Dr. Marcia Betley, University of Wisconsin, Madison, Wis.) is concentrated as for $SEC_1$ and dialyzed.

The toxin is then applied to a carboxymethyl cellulose column. $SEC_2$ is eluted, lyophilized and resuspended in distilled water. The toxin is reapplied to a column of carboxymethyl cellulose and eluted with a linear gradient. The partially purified toxin is concentrated and applied to a Sephadex-G-75 column. The eluted toxin is concentrated and finally reapplied to a Sephadex-G-50 column. Recovery is about 40%, with purity exceeding 99%.

Enterotoxin D (SED)

*Staphylococcus aureus* 1151M (Source: Dr. John Iandolo, Kansas State University, Manhattan, Kans.) is used for the production of enterotoxin B. The medium is similar to that used for SEA and SEB. After growth and removal of the cells, the pH of the supernatant is adjusted to 5.6 and applied to an AmberLite-CG-50 resin. The mixture is stirred for one hour, and the toxin is elute and concentrated using 20% (W/V) polyethylene glycol, 20M. The concentrated toxin is dialyzed and applied to a carboxymethyl cellulose column. The toxin is eluted in a linear gradient and then rechromatographed on carboxymethyl cellulose, The toxin solution is concentrated and chromatographed on Sephadex-G-75. This step is repeated once.

Enterotoxin E (SEE)

*Staphylococcus aureus* strain FRI-236 (Source: Dr. John Iandolo, Kansas State University, Manhattan, Kans.) culture supernatant is concentrated and dialyzed. The toxin is then absorbed to a carboxymethyl cellulose column. The toxin is eluted in a stepwise fashion and concentrated. It is then chromatographed twice on Sephadex-G-75. To obtain highly purified SEE, it is necessary to chromatograph the toxin once more on G-75 in the presence of 6 molar urea.

Enterotoxin F or Toxic Shock Syndrome Toxin-1 (TSST-1). TSST-1a and TSST-1b

Staphylococcus strain MN8 (Source: Dr. Patrick Schlievert, University of Minnesota, Minneapolis, Minn.) is cultured overnight in dialyzable beef heart medium and precipitated from culture fluid by adding 4 volumes of absolute ethanol and storing for at least 2 days. The precipitate is collected by centrifugation and the pellet is suspended in water, recentrifuged and dialyzed to remove salts. The preparation is then electrofocused in a pH gradient of 3–10 using commercial ampholytes with the LKB Multiphor apparatus. The visible band containing TSST-1 is harvested and refocused in a pH 6–8 gradient yielding purified TSST-1.

TSST1a and 1b are isolated by one additional electrofocusing step. After focusing TSST-1 on the pH 6–8 gradient, approximately one-half of the Sephadex gel is removed from the anode end. The gel remaining on the cathode end, containing the TSST-1 band is repoured after the addition of two sore grams of Sephadex gel and then refocused overnight using the remaining pH gradient. After electrofocusing in a pH 6–8 or 6.5–7.5 gradient, protein bands are located by the zymogen print method. Discrete bands are scraped off the plate and eluted with pyrogen free water from the Sephadex gel. Strain MN8 yields approximately 2 mg of each toxin per liter of culture fluid. For *Staphylococcus aureus* strains other than MN8, 200 µg of each toxin is obtained per liter of culture fluid. TSST-1a and 1b are proteins which migrate as homogeneous bands in SDS gels to a molecular weight of 22,000 with isoelectric points of 7.08 and 7.22, respectively.

With the changing technology of protein purification, new methods have been employed for the purification of certain enterotoxins from *Staphylococcus aureus*. Some of these methods are given here.

Enterotoxins A and $C_2$

A 10 ml culture of *Staphylococcus aureus* 11N-165 (SEA), *Staphylococcus aureus* 361 (Source: Dr. John Iandolo, Kansas State University, Manhattan, Kans.) ($SEC_2$) is grown overnight at 37° C. The removal of enterotoxin from the supernatant is carried out using QAE-Sephadex. The toxin is then eluted batchwise from the ion exchanger and recovered by filtration on a sintered glass funnel; The eluates are concentrated by ultrafiltration. The toxin is then passed through a Sephadex G-100 column. Two peaks absorbing at 280 mm are eluted, with the latter containing the enterotoxin. The eluted toxin is concentrated and rerun on Sephadex-100. The overall recovery is about 30% for $SEC_2$ and 40 to 50% for SEA. Both toxins appear homogeneous by sodium dodecylsulfate polyacrylamide gel electrophoresis.

Enterotoxins A, $C_1$, D

This method utilizes fast protein liquid chromatography (FPLC) and high resolution chromatofocusing Mono P column. Enterotoxins in media are concentrated and passed over a Sephadex-G-75 column. The toxin containing fractions are pooled. For $C_1$ and D, the supernatants are passed over an AnberLite-CG-50 column, as described for SED, and the active fractions pooled. All three toxins are then placed in buffer for chromatofocusing and then separated using the MONO P column FPLC system. Since all of the toxins have isoelectric points in the range of 7 to 9, the polybuffer PBE-96 is used for elution. The purity of SEA, $SEC_1$ and SED is estimated to be 98, 95 and 80%, respectively. SEA elutes as two peaks at pH 8.8 and 8.6. $SEC_1$ also elutes as two peaks at pH.8.3 and 7.9, and SED elutes as three peaks at pH 8.6, 8.3 and 8.0.

Enterotoxins may also be produced in mutant strains of *Staphylococcus aureus* by expression of an enterotoxin producing gene in another bacteria or cell. Genetic material which appears to be in the chromosomal plasmid, or phage portion of the bacteria may be used for gene insertion procedures. Complete molecules or fragments with amino acid sequence homology to the parent enterotoxin may be produced with this technology. (Reviewed in Iandolo, J. J., Annu. Rev. Microbial., 43, 375, 1989.) Moreover, mutagenia agents such as N-Nitroso compounds are capable of augmenting significantly the production of enterotoxins by some strains of staphylococcus.

Alpha Toxin

*Staphylococcus aureus* Wood 46 strain (Source: Dr. Sidney Harshman, Vanderbilt University, Nashville, Tenn.) is used and cultured in yeast extract dialysate medium. With the glass-pore bead method undialyzed yeast may be used together with casein, glucose, thiamin and nicotinic acid. The organism is incubated in medium for 24 h at 37° C.

The culture supernatant is applied to a glass-pore bead column and adjusted to pH 6.8. A column of 5×20 cm is used for 3 liter batches and flow rates adjusted to 10–20 ml/min. The column is washed with 0.01M $KHPO_4$ pH 6.8 and then the alpha toxin is eluted with 1.0M $KHPO_4$ pH 7.5. Fractions are tested for the presence of alpha hemolysin by a rapid hemolytic assay using rabbit erythrocytes as substrate.

Streptococcal Pyrogenic Exotoxin (SPE) (Erythrogenic toxin, scarlet fever toxin)

Streptococcus NY-5 strain (Source: ATCC 12351) has been the most widely used for toxin production and studies. A list of various strains to produce toxins A, B, and C has been published. The Kalbach S84 type 3 strain (Source: Dr. Joseph E. Alouf, Institute Pasteur-Unite Associee, Paris, France) is cultured and the supernatant is concentrated and stirred in calcium phosphate gel. Fraction $S_1$ is precipitated with 80% saturated ammonium sulfate. The redissolved pellet is dialyzed and termed Fraction $S_2$. This fraction is precipitated with 50–800% ammonium sulfate, resuspended in phosphate buffered saline (Fraction $S_3$), and gel filtered on a Bio-Gel P-100 column. The fraction corresponding to the volume eluted between 160 and 240 ml is collected and concentrated by ultrafiltration to about 20 ml in an Amicon PM10 Membrane (Fraction $S_4$). Fraction S4 is then submitted to preparative isoelectric focusing (IEF) performed with a 100 ml column. The material which focuses at around pH 4.8 in a narrow peak is collected and dialyzed in an Amicon cell using PBS to eliminate ampholines and sucrose. The Fraction ($S_5$) constitutes purified pyrogenic exotoxin. Another electrophoretic form of SPE with a pI of 4.2 is often separated simultaneously with that of pI 4.8. Both forms show total cross reactivity against immune sera raised by rabbit immunization with fraction $S_3$.

The Fraction $S_5$ shows a single band by SDS-PAGE corresponding to a molecular weight of 28K. Bioassays for determination of activity include erythematosus skin test in rabbits or guinea pigs lymphocyte blast transformation. The toxin may also be detected by enzyme-linked immunoabsorbent assay (ELISA) or hemagglutination inhibition.

Experimental Animal Studies

1. Preparation of Native Enterotoxins

Current methods for purification of all of the enterotoxins utilize ion exchange materials such as CG-50, carboxymethyl-cellulose and the Sephadexes (gel filtration). The preparation of the SEB used for these studies is as follows.

*Staphylococcus aureus* strain I10-275 is cultured in NZ-Amine A media supplemented with 10 gm/liter of yeast extract for 18–20 hours in room air at 37° C. The flank is agitated at 300 RPM. The initial pH of the culture is 6.8 and the postincubation pH 8.0. The culture is filtered through a DC-10 Amicon filter (pore size 0.1 micron). The final filtrate is adjusted to pH 5.6. The filtrate is tested for the presence of SEB in radial immunodiffusion using known antisera to SEB. Eighteen to 20 liters of culture supernatant fluid is diluted with deionized, distilled $H_2O$ (1:5 to 1:10) and the pH adjusted to 5.6 CG-50 resin (Malinkrodt) (800 ml), preequilibrated to pH 5.6 in 0.03 M phosphate butter, pH 6.2 (PB) is added and the mixture stirred for one hour. The resin is allowed to settle and the supernatant fluid decanted. The resin is placed in a column and the toxin eluted with 0.5 M PB, 0.5 M NaCl pH 6.2. The concentrated, dialyzed toxin is placed in a column (5 cm×75 cm) of CM-sepharose (pretreated with 0.005 M PB pH 5.6). The column is washed with the same buffer and the enterotoxin eluted by treating the column stepwise with PB 0.03 M pH 6.0, 0.045 M pH 6.25, 0.06 M pH 6.5 and 0.12 N pH 7.2. The fractions containing the enterotoxin are combined, concentrated with polyethylene glycol (200 cc wet volume of packed resin), and dialyzed against 0.5 M NaCl 0.05 M PH pH 7.2. The concentrated enterotoxin solution (5 ml) is placed in a column of Sephacryl S-200 (pretreated with 0.5 M NaCl, 0.05 M PB, pH 7.2). The column is eluted with the same buffer. The fractions containing the enterotoxin are combined and dialyzed against 0.01 M PB, 0.15 M NaCl pH 7.2. The enterotoxin B concentration is approximately 1 mg/ml. The solution is filter sterilized, frozen and lyophilized. Samples are stored in lyophilized from at 4° C. The final enterotoxin fraction is a white powder which when dissolved in normal saline is a clear colorless solution. Samples containing 5 and 10 $\mu$g/ml are tested in a double diffusion immunoprecipitation assay using known standards of SEB and Mono-specific antisera. A single precipitation line is noted which showed a line of identity with known SEB. Using a tritiated thymidine mitogenic assay with human and murine immunocytes, SEB showed significant mitogenic activity comparable to that of SEA. SEB was found to be devoid of contaminating alpha hemolysin assessed in a rabbit erythrocyte hemolytic assay.

PAGE gel analysis of SEB showed a predominant single band at 28,000 m.w. High performance liquid chromatography (HPLC) profiles were obtained on a MAC PLUS controlling a Rainin Rabbit HPLC with a Hewlett Packard 1040 A Diode array detector and a Vyadac Protein and Peptide C18 column. The profile for purified enterotoxin B was a sharp peak without significant shoulder. There was minimal trace contamination. A functional hemolytic assay for the presence of alpha hemolysin in the pure preparation was negative. Purified enterotoxin batches were negative for endotoxin in the limulus amebocyte lysate assay. The sterility of the preparations was demonstrated by negative cultures in thioglycolate medium and soybean-casein digest. Protein determinations were carried out by a spectrophotometric method.

The sterility of the preparation was demonstrated by negative cultures using (a) fluid thioglycollate medium and (b) soybean-casein digest. A sample containing 1 mg/ml of SEB was tested for endotoxin contamination using sigma E-toxate CAL assay. The final product was found to be free of endotoxin with a standard sensitivity of 0.1 ug endotoxin/mg SEB.

Toxicity testing was carried out in two Hartley strain guinea pigs weighing less than 450 grams, and two female C57 black mice (Simonson Laboratories, Watsonville, Calif.), weighing less than 22 grams. Each animal was observed for 7 days with no significant change in condition or weight after intraperitoneal injection of 0.5 ml of 26 $\mu$g/kg enterotoxin B.

SEA, SEC, SED, SEE, TSST-1 and Streptococcal pyrogenic exotoxin in the studies were prepared by the previously described methods. The identity, purity and sterility of these preparations were tested in a fashion similar to that for SEB.

2. Preparation of Derivatized Enterotoxins

To prepare carboxymethylated enterotoxin B (CM-SEB), 13 mg of purified SEB was dissolved in a solution of 0.4M sodium bromoacetate pH 7.0 and 0.5M potassium phosphate pH 7.0. The solution was incubated in the dark for 14 days at room temperature. At the end of the reaction period, the solution was dialyzed at 4° C. against several changes of sterile distilled water and lyophilized. Amino acid analysis indicated that carboxymethylation of the histidine residues of SEB was complete.

3. Preparation of Synthetic Enterotoxins

A peptide consisting of 26 amino acids corresponding to the N terminal amino acids of SEA, the loop structure of SEA, a conserved mid-molecular sequence of SEA and SEB and a C terminal SEB sequence was synthesized in collaboration with Multi-Peptide Systems, La Jolla, Calif. The preparation of peptides was carried out using a variation of Merrifield's original solid phase procedure in conjunction with the method of simultaneous multiple peptide synthesis using t-Boc chemistries. Peptides were cleaved from the resins using simultaneous liquid hydrogen fluoride cleavage. The cleared peptides Were then extracted with acetic acid and ethyl ether and lyophilized. Reverse phase HPLC analysis and mass spectral analysis revealed a single major peak with the molecular weight corresponding closely to theoretical.

TABLE 10

Class II binding region of SEA

Enterotoxin A loop devoid of Histadine moieties

N terminal Ser-Glu-Lys-Ser-Glu-Glu-Ile-Asn-Glu-Lys-Cys-Ala-Gly-Gly-Tyr

Pro

C terminal Lys-Thr-Val-Gly-Gly-Tyr-Met-Cys-Ala-Thr-Lys-Asn

Conserved sequence (mid-molecule) of enterotoxins A and B

The rationale for the construction of this synthetic peptide is as follows:

(a) Amino acid sequences of enterotoxins A and B known to be involved in the interaction of the native enterotoxins with the T cell receptor and class II molecules are retained.

(b) The loop structure of enterotoxin A is retained because it is devoid of histadine moieties which are known to be associated with the emetic response.

(c) Amino acids 1–10 in the N-terminal region of enterotoxin A are retained because they have been shown to have class II binding activity.

(d) The loop structure of enterotoxin A was retained because both the loop and associated disulfide linkages were considered to be important for T lymphocyte mitogenicity, stabilization of the molecule and resistance to in vivo degradation.

(e) A conserved sequence in the central portion of enterotoxin A and B adjacent to the disulfide loop (amino acids 107–114) was retained.

(f) Histadine moieties are deleted from the molecule because of their association with the emetic response.

4. Preparation of Vehicle—Adjuvant Formulation

The vehicle was prepared as follows: To phosphate buffered saline (PBS) containing 0.4% (v/v) Tween 80, was added 5% (v/v) Pluronic 121 and 10% squalene. This mixture was vortexed vigorously to produce a uniform emulsion. One volume of this vehicle mixture was then added to an equal volume of enterotoxin dissolved in PBS and vortexed briefly to ensure complete mixing of components. The final concentrations were (v/v): 0.17% Tween 80, 2.5% Pluronic L121, 5% squalene. A total of 2 ml of this mixture containing various concentrations of toxins was injected intramuscularly into thigh muscles of rabbits bearing VX-2 carcinoma.

5. Preparation of Soluble Ibuprofen

Ibuprofen (Sigma, St. Louis, Mo.) 800 mg was added to solution containing 30 ml of distilled water, 6 ml of 1N $N_aOH$ and 50 mg of $N_aPO_4$. The solution was vortexed vigorously. The pH was adjusted to 7.1–7.8 with 1N HCl added dropwise. Sterile distilled water was added to a final volume of 40 ml. The solution containing 20 mg/ml of Ibuprofen was stored at −20° C.

6. Animals

New Zealand white female rabbits weighing from 2.5 to 5.0 kg, ages 2 to 4 months were used for studies employing purified enterotoxins. Rabbits of higher weight were used in preliminary studies which are discussed in application Ser. No. 07/416,530, filed on Oct. 3, 1989. The animals were obtained from the Elkhorn Rabbitry, Watsonville, Calif.

7. Tumor

The tumor used for these studies was obtained from the Frederick Cancer Research Facility of the National Cancer Institute. It was stored frozen in the DCT tumor repository. The tumor call lettered G50014 was also known as the VX-2. Stewart, H. L., Snell, K. C., Dunham, L. J.: Transplantable and transmissible tumors of animals. In Atlas of Tumor Pathology. Washington, D.C., Armed Forces Institute of Pathol., pp. 38, 355, 1959. The tumor is a carcinoma indigenous to the New Zealand white rabbit. It was stored as a tissue fragment, and suspended in saline. The tumor was initially induced by shope virus and derived from a transformed papilloma in a dutch belted rabbit. Kidd and Rous described the tumor in 1937. Histopathologioallys the tutor consists of cords and sheets of epithelial cells (80%) and 20% hemorrhage and necrosis with no acini. The growth is primarily papillary. Numerous mitoses are evident. The cells are thin walled and very anaplastic. The tumor used was cryopreserved from Oct. 20, 1985. It had a negative viral profile.

8. Tumor inoculation

Tumor fragments for inoculation were obtained from VX-2 growing in rabbit thigh. Fragments were implanted intramuscularly into the right thigh of recipients. Donors were placed under general anesthesia with halothane (1.5%) and under sterile conditions, small fragments were excised and placed in Dulbecco's Modified Eagles Medium with glutamine (Gibco Life Technologies, Inc., Grand Island, N.Y. 14072). The fragments were rinsed and then suspended in media until they were transferred into new hosts. Recipient rabbits had their right thigh shaved and scrubbed with alcohol and betadine. A small area was anesthetized with 1% lidocaine. With a scalpel, an incision was made through the skin into the muscle where a small pocket was created. With forceps, 4 to 5 tumor fragments were implanted into the muscle. The wound was closed with 1 or 2 nylon sutures. Tumors appeared at the implantation site within 4 weeks and therapy was started when the tumors were at least 1 to 2 centimeters in broad diameter.

9. Tumor Measurements

Tumors were measured by calipers by a certified veterinary oncologist before and At intervals after treatment. Complete remission was present when there was no evident tumor. Partial remission represented a reduction of tumor volume by greater than 50%. Less than partial remission was a 25–50% reduction in tumor volume.

10. Conditions of Administration

Various enterotoxins, Streptococcal pyrogenic exotoxins, carboxymethylated enterotoxin B, or synthetic enterotoxins in lyophilized form were diluted in 0.9% saline or sterile distilled water and then filtered through a 0.45 micron Millipore filter. Aliquots were stored at −20° F. Each aliquot was thawed once, used only for a single injection and then discarded. Various preparations in appropriate dose were prepared in 1 ml of 0.9% saline and drawn up in a 1 ml syringe. This solution was administered via the central ear vein which was cannulated with a 25 gauge needle and attached infusion tubing (Butterfly, 25×¾ with 12" tubing set, Abbott Hospital, N. Chicago, Ill. 50064). Following venous cannulation, tubing and needle were washed with saline using a 3 ml syringe and, with the tubing filled with saline, the toxin infusion was begun using a 1 ml tuberculin syringe (Monoject tuberculin 1.0 cc, Division of Sherwood Medical, St. Louis 63103). Approximately 0.3 ml of toxin was administered per minute. The tubing and needle were washed with 6 ml of normal saline over an additional 3 minutes using a 3 ml syringe.

11. Enterotoxin Administration to Tumor Bearing Rabbits

Studies in 20 rabbits using partially purified enterotoxin B as a single dose of 100–150 μg/kg or 40–60 μg/kg resulted in tumor regressions. With a dose of 40–60 μg/kg, six of twelve animals showed objective tumor regressions while a dose of 100–150 μg/kg resulted in objective tumor responses in three of nine rabbits treated. Results of these studies are given in prior applications. Ser. No. 07/416,530 filed on Oct. 2, 1989 and Ser. No. 07/466,577, filed on Jan. 17, 1990. Toxicity of these preparations was thought to be due to contaminating elements in particular staphylococcal alpha hemolysin. Accordingly, the next phase of these studies was carried out with purified enterotoxin B.

a) Purified Enterotoxin B

Purified enterotoxin B in a mean dose of 26 μg/kg was administered to seven animals on one, two or three occasions (Table 11). Five showed complete remissions while one additional rabbit demonstrated 96% regression. One showed tumor progression. Of the four animals receiving a mean dose of 13 μg/kg, one had a complete remission while three showed tumor progression. A single animal given a dose of 40 μg/kg died within 12 hours of injection. Six of eight animals with major regressions showed enduring responses lasting 2 to 6 months without evident tumor recurrence (Table 11).

b) Purified Enterotoxin A

SEA in a dose of 0.9 μg/kg was given to 5 rabbits on two or three occasions. Two showed complete remissions while three others demonstrated tumor progression (Table 12). and one died acutely after the third injection. SEA in a dose range of 5–12 μg/kg was administered to 7 animals. Two achieved complete remission while one experienced a 60% remission. Four others died acutely after the first injection.

c) Carboxymethylated Enterotoxin B (CM-SEB)

Five rabbits were with VX-2 carcinoma treated with CM-SEB in doses of 26 μg/kg or 40 μg/kg on days 0, 4 and 11. Two animals showed complete remissions of their tumor within sixty days after the last injection while three animals showed tumor progression. The two complete remissions have been sustained for more than one year (Table 13).

d) Streptococcal Pyrogenic Exotoxin (SPEA)

Studies have now been initiated in rabbits with VX-2 carcinoma using intravenously administered Streptococcal pyrogenic exotoxin in a dose of 13 μg/kg. Two animals have shown complete remission while a third has had tumor progression (Table 14).

e) Purified TSST-1

Two rabbits with VX-2 carcinoma have been treated with 0.5 μg/kg of TSST-1. One showed a complete remission over 40 days while a second showed tumor progression.

f) Purified Enterotoxins C, D and E

Studies have now been initiated in rabbits with VX-2 carcinoma using intravenously administered enterotoxins C, D, and B.

g) Enterotoxins in Vehicle-Adjuvant Preparations

Studies have now been initiated using various enterotoxins incorporated in vehicle-adjuvant formulations as prepared above and injected into rabbits with VX-2 carcinoma.

h) Synthetic Enterotoxins.

Studies have been initiated in rabbits with VX-2 carcinoma using intravenously administered synthetic enterotoxins as prepared above.

i) Untreated Control Animals

Five rabbits were inoculated with the VX-2 carcinoma as given above but were not treated with enterotoxins. All five showed progressive tumor growth over 90 days observation. No spontaneous remissions of tumor were observed.

TABLE 11

Purified Enterotoxin B (Lot TTB-16)

| Animal Number | Maximum Response | Time to Maximum Response (days) |
|---|---|---|
| | Mean Dosage 26 μg/kg | |
| QT[2] | complete remission | 24 |
| Wanda[1] | complete remission | 20 |
| Cindy[2] | complete remission | 30 |
| Edna[2] | complete remission | 46 |
| Magnolia[3] | complete remission | 75 |
| Periwinkle[3] | 96% | 68 |
| Heidi[2] | progression | |
| | Mean Dosage 13 μg/kg | |
| KT[1] | complete remission | 14 |
| Dinky[2] | progression | |
| Mazie[2] | progression | |
| Gretta[1] | progression | |
| | Mean Dosage 40 μg/kg | |
| Bonnie[1] | NC | 12 hours (acute death) |
| | Untreated | |
| Gardenia | progression | |
| Rachel | progression | |
| Elyce | progression | |
| Z-1 | progression | |
| Z-2 | progression | |
| A-4 | progression | |

[1]One injection on day 0.
[2]Two injections: One injection on day 0 and one injection on days 4, 5, 7 or 8.
[3]Three injections: One injection on day 0, one injection on days 4 or 6, and one injection on days 11 or 13.

TABLE 12

Purified Enterotoxin A[1]

| Animal Number | Maximum Response Mean Dosage 0.9 μg/kg | Time to Maximum Response (days) |
|---|---|---|
| Poppy | complete remission | 47 |
| Mallory | complete remission | 120 |
| Jennifer | progression | |
| Stephen | progression | |
| Alex | progression | |

[1]Animal received a total of three injections given on day 0, 4 or 6 and 10 or 11 or 12 or 13 or 15.

TABLE 13

Carboxymethylated Enterotoxin B[1]

| Animal Number | Maximum Response | Time to Maximum Response (days) |
|---|---|---|
| | Mean Dosage 26 or 40 μg/kg | |
| Z-4 | complete remission | 40 |
| Z-5 | complete remission | 60 |
| Z-3 | progression | |
| A-1 | progression | |
| A-2 | progression | |

[1]Animals received a total of three injections given on days 0, 4 and 10 or 11 or 12.

TABLE 14

Purified Streptococcal Pyrogenic Enterotoxin A[1]

| Animal Number | Maximum Response | Time to Maximum Response (days) |
|---|---|---|
| | Mean Dosage 13 μg/kg | |
| E3 | complete remission | 17 |
| E6 | complete remission | 13 |
| E1 | progression | |

[1]Animals received a total of two injections given on day 0, 7 or 10.

12. Long Term Responses and Follow-Up of Responder Animals Treated With Enterotoxin B Six of seven animals with tumor remission showed no tumor recurrence over observation periods of three weeks to three months after documented complete remissions. One animal showed tumor recurrence at the primary site appearing within one week after a 96% regression. Two animals died of pneumonia three weeks and 2.5 months, respectively, after tumor regressions. Autopsies of both showed no evidence of tumor recurrence (Table 15).

TABLE 15

FOLLOW-UP AFTER REMISSIONS

| Animal | Length of Follow-Up After Remission | Condition of Animal |
|---|---|---|
| QT | 3 months | Excellent. No recurrent tumor. |
| Wanda | 6 weeks | Excellent. Cage injuries. euthanized. No recurrent tumor. |
| Cindy | 2 months | Excellent. No recurrent tumor. |
| Edna | 2 months | Excellent. No recurrent tumor. |
| Magnolia | 2.5 months | Excellent until pneumonia (death) Autopsy: No recurrent tumor. |
| KT | 3 weeks | Excellent until pneumonia (death) Autopsy: No recurrent tumor. |
| Periwinkle | 2 months | Recurrent tumor at primary site. |

13. Toxicity of Enterotoxins

With SEB in doses of 10 to 26 μg/kg, all animals showed anorexia, mild weight loss and temperature elevations of 1–4° F. above baseline for 24 hours after treatment. Following this point all animals stabilized and temperature normalized while most steadily gained weight over the ensuing weeks as tumors regressed. Toxicity is given in Tables 16 and 17. In contrast, control untreated animals showed progressive tumor growth associated with steady weight loss. Rabbits with longstanding survival after remissions showed no long-term toxicity except for pneumonia which developed in two. Autopsy results and histologies of three tumor bearing rabbits and three control animals are given in Tables 17, 18, and 19.

Five of seven rabbits given enterotoxin A in doses of 5–12 μg/kg died within 72 hours of the first dose. However, when the dose was reduced to 0.9 μg/kg four of five animals survived with two showing complete remission and one dying after the third injection. The animals showed temperature elevations of 2° to 5° F. and anorexia for 1–3 days after injection. During acute inflammatory activity in the tumor, animals often lost weight.

With carboxymethylated SEB in doses of 26 μg/kg and 40 μg/kg, there was no significant toxicity. Mild temperature elevations were noted but there was no significant anorexia or weight loss.

With streptococcal pyrogenic exotoxin A, animals showed mild temperature elevations and anorexia for 1–2 days after injections. One animal died after 3 days after the second injection on day 10.

TABLE 16

TOXICITY IN SEB TREATED RABBITS
Acute Toxicity

| Rabbit No. | Maximum Temperature Elevations (degrees F.) | Maximum Acute Weight Change (lbs.) | Appetite and General Behavior |
|---|---|---|---|
| QT | 3.8° | −1 | Anorexia for 2 days after Rx. |
| Wanda | 3.6° | −1.25 | Anorexia for 2 days after Rx. Subdued. |
| KT | 4.4° | −2.1 | Anorexia for 2 days after Rx. Subdued. |
| Cindy | 1.6° | −0.3 | Anorexia for 2 days after Rx. Subdued. |
| Periwinkle | 2.8° | −0.9 | Anorexia for 2 days after Rx. Subdued. |
| Magnolia | 3.0° | −0.14 | No anorexia. Normal activity. |
| Edna | 2.6° | −0.4 | No anorexia. Normal activity. |

TABLE 17

TOXICITY IN SEB TREATED RABBITS
Long Term Effects

| Rabbit No. | Temperature (degrees F.) | Maximum Long-Term Weight Change (lbs.) | Appetite and General Behavior |
|---|---|---|---|
| QT | Baseline | no change | Excellent appetite and behavior. |
| Wanda | Baseline | −1.2 | Excellent appetite and activity. |
| KT | Spiking temperature | −1.6 | Excellent appetite and activity. |
| Cindy | Baseline | +3.0 | Excellent appetite and activity. |
| Periwinkle | Baseline | +2.1 | Excellent appetite and activity. |
| Magnolia | Baseline | +3.6 | Excellent appetite and activity. |
| Edna | Baseline | +1.6 | Excellent appetite and activity. |

TABLE 18

SEB-TREATED RABBITS - AUTOPSY FINDINGS

| Rabbit No. | Lungs | Liver | Spleen | Kidneys | Intestine | Heart | Tumor |
|---|---|---|---|---|---|---|---|
| KT | Pneumonia | NGL* | NGL | NGL | NGL | NGL | No tumor evident. |
| Magnolia | Pneumonia | NGL | NGL | NGL | NGL | NGL | No tumor evident. |
| Periwinkle | Pneumonia | NGL | NGL | NGL | NGL | NGL | Tumor progression at primary site. |

*NGL: No gross lesions.

TABLE 19

| SEB-TREATED RABBITS - HISTOLOGIC FINDINGS | | | | |
|---|---|---|---|---|
| Rabbit No. | Lungs | Liver | Spleen | Kidneys |
| KT | Pneumonitis | WNL | WNL | WNL |
| Magnolia | Pneumonitis | WNL | WNL | WNL |

TABLE 20

| UNTREATED RABBITS - AUTOPSY FINDINGS | | | | | | | |
|---|---|---|---|---|---|---|---|
| Rabbit No. | Total Weight Loss (lbs.) | Lungs | Liver | Kidneys | Intes-tine | Spleen | Heart |
| Elyce | 1.3 | NGL | Nodules | Nodule (R) | NGL | NGL | NGL |
| Gardenia | 2.0 | NGL | NGL | NGL | NGL | NGL | NGL |
| Pearl | 1.6 | NGL | NGL | NGL | NGL | NGL | NGL |
| A-4 | 1.0 | NGL | NGL | NGL | NGL | NGL | NGL |
| Z-1 | 1.8 | | | | | | |
| Z-2 | 1.4 | | | | | | |

14. Histology

Microscopically, tumors showed extensive hemorrhagic necrosis in samples obtained 12 to 72 hours after the initial injection. Control untreated tumor showed focal areas of necrosis within the tumor, but no areas of hemorrhagic necrosis. Indeed the areas of necrosis were far more extensive in the treated tumors with few if any areas of viable tumor. In the treated tumors, small blood vessels demonstrated hemostasis, and focal areas of inflammatory cell extravasation in the perivascular area. These changes were not seen in control untreated tumor specimens.

15. Multiple Injections of Enterotoxins Induce Antitumor Effects

Tumor bearing rabbits were given two or three injections of SEB, C-SEB, SEA or TSST-1 and showed tumor regressions. It is known that enterotoxins induce production of various cytokines and that one such cytokine namely interferon will in turn upregulate the surface expression of IA molecules and Class II major histocompatibility antigens. Such additional upregulated antigen presenting cells, would be further capable of binding additional enterotoxins and presenting them to the T lymphocyte repertoire. Moreover, a synergy has been noted between various cytokines namely tumor necrosis factor, interferon and various mitogens for T lymphocyte activation. Therefore, we may speculate that in the presence of various cytokines induced by the first injection of enterotoxins, upregulated antigen presenting cells are prized to bind additional toxin given in the second or third injection producing substantially augmented T cell proliferative responses and associated anti-tumor effects.

It is conceivable that the enterotoxins might be employed together with various cytokines such as IL-2 in vitro to develop a highly enriched population of T lymphocytes that could subsequently be injected at various intervals to continuously augment the anti-tumor effect in tumor bearing hosts.

Finally, while the enterotoxins were given intravenously in the present experiments, it is quite conceivable that the toxins could be administered in adjuvant form bound to vehicles such as aluminum hydroxide, liposomes, water in oil emulsions, pluronic triblock polymers and saponin with similar anti-tumor effects.

16. Attenuation of Toxicity with Ibuprofen

The administration of Ibuprofen (20 mg/ml) given in doses of 0.25 to 0.5 ml subcutaneously when temperatures reached 105° F. or greater resulted in reduction in fever by 2 to 5° F. Ibuprofen could be administered every 4 to 6 hours; however, in general, it did not need to be given more than once or twice per 24 hours. The use of this drug did not interfere with the observed tumor reduction or histologic hemorrhagic necrosis.

Ibuprofen may inhibit the prostaglandin mediated effects of the inflammatory cytokines including fever and anorexia but does not affect other antitumor immune and inflammatory responses.

Ibuprofen is only one of a large group of drugs known as non-steroidal anti-inflammatory agents (cyclooxygenase and prostaglandin synthesis inhibitors), which would also be useful to attenuate toxicity induced by the enterotoxins.

17. Genetic Aspects of Enterotoxin Production

Proceeding from the seminal work of Cohen & Boyer, U.S. Pat. No. 4,237,224, DNA technology has become useful to provide novel DNA sequences and produce large amounts of heterologous proteins in transformed cell cultures. In general, the joining of DNA from different organisms relies on the excision of DNA sequences using restriction endonucleases. These enzymes are used to cut donor DNA at very specific locations, resulting in gene fragments which contain the DNA sequences of interest. These DNA fragments usually contain short single-stranded tails at each end, termed "sticky-ends". These sticky-ended fragments can then be ligated to complementary fragments in expression vehicles which have been prepared, e.g., by digestion with the same restriction endonucleases. Having created an expression vector which contains the structural gene of interest in proper orientation with the control elements, one can use this vector to transform host cells and express the desired gene product with the cellular machinery available. Once expressed, the gene product is generally recovered by lysing the cell culture, if the product is expressed intracellularly, or recovering the product from the medium if it is secreted by the host cell.

Recombinant DNA technology has been used to express entirely heterologous gene products, termed direct expression, or the gene product of interest can be expressed as a fusion protein containing some parts of the amino acid sequence of a homologous protein. This fusion protein is generally processed post-translationally to recover the native gene product. Many of the techniques useful in this technology can be found in Maniatis, T., at al., *Molecular cloning: A Laboratory Manual*, Cold Spring Harbor Laboratory, New York (1982).

However, while the general methods are easy to summarize, the construction of an expression vector containing a desired structural gene is a difficult process and the successful expression of the desired gene product in significant amounts while retaining its biological activity is not readily predictable. Frequently gene products are not biologically active when expressed in yeast, bacteria or mammalian cell systems. In these cases, post-translational processing is required to produce biological activity.

From physical and genetic analysis, the genes for SEA, SEB, SEC, and SEE occupy a chromosomal loci. The structural gene encoding SED in all strains examined is localized, to a large penicillinase-like plasmid.

The enterotoxin A gene has been cloned. SEA was expressed in the *E. coli* genetic background from a single 2.5 kbp Hind III chromosomal DNA fragment. When sequenced, the DNA was found to contain a single reading frame that generated a protein consistent with the partial sequences of SEA derived by chemical methods. Therefore, it is apparent that the site mapped contained the structural gene for SEA. Betley, M. J., Mekalanos, J. J., J. Bacteriol, 170, 34, 1987; Huang, I. Y., Hughes, J. L., Bergdoll, M. S., Snchantz, E. J., J. Biol. Chem., 262, 7006, 1987; Betley, M., Lofdahl, B., Kreiswlrth, B. H., Bergdoll, M. S., Novick, R. P. Proc. Natl. Acd., Sci., USA, 61, 5179, 1984.

The enterotoxin A gene was found to be at least 18 kilobases in length and was carried on a mobile element. Enterotoxin A production was linked to the presence of a bacteriophage which integrates into the bacterial chromosome. The enterotoxin A gene is located near the phage attachment. The enterotoxin A gene was mapped between the purine and isoleucine-valine markers in 24 *Staphylococcus aureus* strains. Conversion to the SEA producing phenotype was induced by lysogenization with a temperate phage purified from *Staphylococcal aureus* strain PS42D. Therefore, a bacteriophage vector was found to be responsible for the toxin phenotype in suitable recipients.

The enterotoxin B gene has been cloned and expressed in *E. Coli*. The DNA of the gene derived from *E. Coli* has been sequenced and matches the chemically derived sequence with only minor differences. Gaskill, M. E., Khan, S. A., J. Biol. Chem., 263, 6276, 1988; Jones, C. L., Khan, S. A., J. Bacteriol, 166, 29, 1986; Huang, I. Y., Bergdoll, M. S., J. Biol. Chem., 245, 3518, 1970.

The SEC gene has been cloned from the chromosome of *Staphylococcus aureus* MN Don. The cloned toxin was expressed in *E. coli* with a molecular weight comparable to that of the toxin from *Staphylococcus aureus*. The toxin was biologically active as measured by pyrogenicity, enhancement of lethal endotoxic shock and mitogenicity with murine splenocytes. The DNA sequence of the enterotoxin C gene has been developed and a protein sequence derived that compares favorably with the complete chemical sequence reported earlier. Bohach, G. A., Schlievert, P. N., Infect Immum., 55, 428, 1987; Bohach, G. A., Schlievert, P. M. Mol. Gen. Genet. 209, 15, 1987.

The entotoxin D gene has been found to occur on a 27.6 kbp plasmid. The enterotoxin D gene has been cloned an expressed in *E. coli* and other Staphylococcal strains. The enterotoxin D gene in *Staphylococcus aureus* is under control of the agar locus like most Staphylococcal extracellular protein genes. The DNA sequence was determined encoding a mature protein with amino acid composition and reaction with antibody to SED confirming its identity to the biochemically purified toxin. Couch, J. L., Saltis, M. T., Betley, M. J., J. Bacteriol. 170, 2954, 1988.

The enterotoxin E gene has been cloned from *S. Aureus* FR1918 and was expressed in *E. coli* encoding an extracellular protein of 26,425 daltons. Its identity to SEE was confirmed immunologically and by correspondence of N terminal and C terminal analysis. Kreiswirth, B. N., Lofdahl, S., Betley, M. J., O'Reilly, Schlievert, P. M. Nature, 305, 709, 1983.

TSST-1 gene was not associated with either bacteriophage or plasmid DNA. The gene was cloned on a 10.6 kbp fragment of chromosomal DNA and subsequently on an approximately 1 kbp subclone of the larger fragment. The TSST-1 gene was expressed in *E. Coli*, and TSST-1 was secreted into the periplasm. The genetic element coding for TSST-1 was found to occupy two loci on the Staphylococcus genome. The loci are indicated by the notation Hi 555; one is at the junction of regions 1 and 2 and is indistinguishable from att012 and closely linked to tyrB. The second is within the trp operon at the junction of regions 17 and 18. Hi555 encodes the tst gene and is a heterologous insertion element that provisionally exhibits some of the characteristics of a transposon. Strains that are $Trp^-$ contain Hi555 at regions 17 and 18 (linked to Trp), while strains that are $Trp^+$ contain Hi555 elsewhere linked to TryB. However, the $Trp^-$ phenotype is not due to insertional inactivation by the unusual element. The sequence and analysis of the tst gene has been described. It codes for a mature protein (TSST-1) of 197 amino acids and a molecular weight of 22,049. Cooney, J., Mulvey, M., Arbuthnott, J. P., Foster, T. J., J. Gen. Microbiol., 134, 2179, 1988.

Streptococcal pyrogenic exotoxin (SPEA) is clearly related to the enterotoxins. It has a cysteine loop of 9 amino acids similar to that of SEA and is also encoded by a converting phage. SPEA shows greater amino acid sequence similarity with SEB than SEA. Immunologic studies show that the proteins and antisera to either enterotoxin are cross reactive. Therefore, genes for all of the enterotoxins have been isolated and transfected into other bacteria to obtain selective production. These genes may be used as sources of accelerated production of these toxins in high producing bacteria employing transfection techniques familiar to one skilled in the art. Iandolo, J. J., Annu. Rev. Microbiol., 43, 375, 1989.

High producing strains of Staphylococcus for selective enterotoxin production have been identified and are available as described in enterotoxin purification section above. Moreover, exposure to mutagenic agents such as N-methyl-N'-nitro-N-nitrosoguanidine of enterotoxin producing *Staphylococcus aureus* has resulted in a 20 fold increase in enterotoxin production over the amounts produce by the parent *Staphylococcus aureus* strain. Freedman, M. A., Howard, M. B., J. Bacteriol, 106, 289, 1971.

18. Enterotoxin Genes: Genetically Engineered Tumor Cells, Accessory Cells, and Peptides The genes for the enterotoxins and streptococcal pyrogenic exotoxin have been cloned. With their known mimicry of the Mls locus and their affinity for that transfection of the enterotoxin gene into tumor cell bearing appropriate HLA-DQ or DR or DP would result in production of a tumor cell bearing the minor lymphocyte stimulating locus capable of ligating MHC class II molecules with T lymphocytes, therefore stimulating potent T cell proliferation and associated antitumor immunity. Experiments are being designed and implemented to test this hypothesis. The rabbit VX-2 carcinoma cells have been established in tissue culture. The gene for enterotoxins A and B have been isolated and have been made available for these studies by Dr. Marcia Betley and Dr. Saleem Khann, respectively. Plans for transfection of rabbit VX-2 carcinoma cells with both genes have been made with Dr. Susan Faas and Dr. John McIntyre of Tektagen, Malverne, Pa. The transfected cells will then be injected into rabbits bearing the VX-2 carcinoma with appropriate controls consisting of non-transfected rabbit VX-2 carcinoma cells and VX-2 cells transfected with an irrelevant microbial gene. Anti-tumor effects will be assessed in this system.

Alternatively, the toxin gene transfected tumor cells could be used for in vitro stimulation of host immunocytes prior to or coordinate with the addition of interleukin 2 to produce an enriched population of tumor specific T cells which could then be reinfused into a tumor bearing host and would be expected to exert tumor killing effects.

The enterotoxin gene could be used to transfect various accessory cells resulting in enterotoxin expression on the cell surface which may then induce more potent stimulation and proliferation of tumoricidal T lymphocytes. The cotransfection of these accessory cells with adhension molecules and MHC molecules might further augment the mitogenic activity of T lymphocytes induced by these accessory cells.

Mutant genes of the toxins could be used to transfect various bacteria such as *E. Coli* resulting in the production of toxin peptides retaining antitumor activity. Such superantigen peptides might have sequences homologous with various naturally occurring viruses such as mammary tumor virus, endogenous proteins such as heat shock proteins, stress proteins and minor lymphocyte stimulating loci, naturally occurring bacteria such as mycoplasma and mycobacterial species. Amino acid sequences in the native toxin molecules associated with toxicity such as emesis, excessive cytokine induction or humoral antibody production would be deleted. For example, histadine residues of SEB may account for emetic responses of the SEB molecule since carboxymethylation of the SEB molecule selectively blocks histadine moieties resulting in a reduction of the emetic response. Additional mutant genes might be employed to produce peptides which bind selectively to T lymphocytes or class II molecules without stimulating mitogenesis, cytokine or antibody production. As such, these genetically engineered molecules might be used to block or eliminate autoimmune responses induced by proliferation of clones of immunocytes reactive to self constituents such as basic myelin protein in multiple sclerosis or synovial constituents in reheumatoid arthritis.

Moreover, enterotoxin genes would be fused with genes from other bioreactive compounds such as cell poisons to produce molecules with capacity to destroy a selective cell population. Such fusion peptides might include enterotoxin sequences fused, for example, with peptides of pseudomonas toxin, diphtheria toxin sequences or antibodies yielding complexes retaining the major structural, biologic features of the native proteins.

19. Bacterial Products Related to Staphylococcal Enterotoxins with Similar Biological Effects Streptococcal pyrogenic exotoxin (SPE) is produced by many strains of group A streptococci. Three antigenically distinct types (A, B, C) have been described. It is now known that Streptococcal pyrogenic exotoxin or scarlet fever toxin is related to *Staphylococcus aureus* enterotoxin B. The amino acid sequence of SPE has significant homology with *Staphylococcus aureus* enterotoxin B but not with other proteins in the Dayhoff library. Table 20 shows the alignment of amino acid sequences of mature SPEA and *Staphylococcus aureus* enterotoxin B, as reported in Johnson, L. P., L'Italien, J. J. and Schievert, P. M. "Streptococcal pyrogenic exotoxin type A (Scarlet fever toxin) is related to *Staphylococcus aureus* enterotoxin B," Mol. Gen. Genet (1986) 203:354–356.

The biological properties of SPE are shared with some staphylococcal enterotoxins such as lymphocyte mitogenicity, fever induction and enhanced susceptibility to endotoxin shock when given intravenously. SPE activates murine T cells mainly $V_\beta 8.2$ in physical association with MHC class II molecules expressed on accessory cells. SPE causes deregulation of the immune response in vitro resulting in delayed (12–16 days) acceleration of humoral and cellular immune activity. This may account for the sustained anti-tumor responses noted with the use of its structural analog, namely enterotoxins B, when administered to rabbits with the VX-2 carcinoma as demonstrated herein. Moreover, SPE has now been shown to induce a toxic shock like syndrome identical to that associated with various enterotoxins. Given the biological and structural relatedness of these proteins, it would be anticipated that SPE and any other protein, bacterial or otherwise, with homology to enterotoxins would produce tumoricidal effects identical to those of enterotoxins. Indeed, this prediction was borne out by demonstrating complete tumor remissions in the first two of three rabbits bearing large VX-2 carcinomas treated with intravenously administered SPEA.

20. Enterotoxins and Homologous Potential Vaccines for Treatment of Cancer and Autoimmune Disease In an attempt to develop safer and more effective methods of administering enterotoxins to tumor bearing hosts, a hybrid molecule was synthesized representing structures common to both enterotoxins A and B. The molecule contained 26 amino acids and had many structural features as delineated above.

This hybrid was administered both intravenously and in adjuvant form to tumor bearing hosts, namely rabbits with VX-2 carcinoma. The adjuvant used for these studies was the pluronic acid triblock copolymer which has been used to boost the immune response to various antigens in animal models and which is under testing at this point in humans with hepatitis and herpes simplex infections. While we have used this adjuvant specifically, it is anticipated that other adjuvant-vehicle preparations might work, including those prepared in water and oil emulsion and aluminum hydroxide.

While we have incorporated the hybrid molecule given herein in adjuvant, additional enterotoxin hybrid molecules containing amino acid sequences homologous to the enterotoxin family would also be effective in this system. To this extent, mammary tumor virus sequences, heat shock proteins, stress peptides, mycoplasma and mycobacterial antigens and minor lymphocyte stimulating loci bearing tumoricidal structural homology to the enterotoxin family would also be useful in this application as anti-tumor agents. Hybrid enterotoxins and other sequences homologous to the native enterotoxins might be immobilized or polymerized genetically or biochemically to produce the repeating units and stoichiometry required for (a) binding of accessory cells to T lymphocytes and (b) activation of T lymphocytes.

It is now recognized that various enterotoxins, toxin analogues and superantigens can activate the autoimmune response. For example, SED is now known to stimulate the production of human rheumatoid factor and mycoplasma arthritidis a well-known superantigen is recognized as the causative agent in murine adjuvant arthritis. Moreover, it is now recognized that various other diseases such as multiple sclerosis are caused by the activation of T lymphocytes (bearing $V_\beta$ receptors) with specificity for multiple self components. In the case of the autoimmune response directed to basic myelin protein, the receptors for activation of T lymphocytes could be readily blocked by various enterotoxin fragments which retain specificity for the T cell receptor but do not initiate T cell activation or mitogenesis. The enterotoxins possess multiple amino acid motifs that are avid for various portions of the T cell $V_\beta$ repertoire, These sequences on the N or C terminal portion of the molecules would bind to autoreactive T lymphocytes and therefore inactivate these clones by blocking further antigenic stimulation and mitogenesis. Indeed blocking of mitogenesis induced by intact native enterotoxins was demonstrated when an N terminal 26 amino acid sequence of enterotoxin A was preincubated with accessory cells. Additional other toxin fragments could be so utilized in vivo. It is conceivable that radionuclides or other cellular toxins attached to the enterotoxin fragments could also be used to eliminate such autoreactive clones.

Moreover, enterotoxins are as potent superantigens may be employed for stimulation of protective anti idiotype B and T cell clones resulting in production of anti-idiotype antibodies that would then block proliferative activity and/or antibody production by auto-reactive lymphocytes.

21. Staphylococcal Enterotoxin Peptides with Biologic Activity

Studies of amino acid homology of Streptococcal pyrogenic exotoxin and enterotoxin B have suggested that there may be biologically active fragments present within the whole molecule. Indeed, cyanogen bromide generated toxin fragments of TSST-1 have been shown to be responsible for T lymphocyte mitogenicity and suppression of immunoglobulin synthesis. These functions could be selectively blocked by monoclonal antibodies directed to the respective fragments. Amino acid analysis of the toxins show that they contain similar domains that may give rise to mitogenic and emetic properties in susceptible cells. A peptide fragment in SEC was shown Spero and Morlock to contain the active sites for emesis and diarrhea. The mitogenic region resided in the C terminal tryptic fragment of SEC.

An immune functional site on Staphylococcal enterotoxin A has been identified corresponding to residues 1–27 of SEA which is responsible for stimulation of T cell proliferation and induction of interferon-y. This SEA (1–27) sequence corresponds to N-Ser-GIv-Lys-Ser-Glu-Glu-Ile-Asn-GFlu-Lys-Asp-Lev.Arg Lys-Lys-Ser-Glu-Leu-Gln-Gly-Thr-Ala-Lev-Gly-Asn-Lev-Ly and blocks SEA induced T cell proliferation and production of interferon y which was not seen with SEA (28–48) peptide. Thus, a functional site on SEA responsible for modulation of T cell function involves the N-terminal 27 amino acids. These molecules may interact at either the level of TCR or the binding of SEA to class II MHC antigens.

For TSST-1, mitogenic activity was shown to be located on a 14,000 dalton cyanogen bromide generated toxin fragment. Other studies using proteolytic digestion of the TSST-1 with papain demonstrated mitogenic activity in 12,000 dalton fragment occupying ⅔ of TSST-1 molecule toward COOH terminal end of holotoxin. On the other hand, non-specific mitogenicity of rabbit lymphocytes demonstrated by enterotoxins A, B, and $C_1$ was associated with the N terminal ends of the molecules.

The emetic reaction and a related immediate-type skin reaction to SEB appears to be mediated by histamine and cysteinyl leukotrienes, liberated from mast cells. Enterotoxins probably act on intramucosal or intradermal ganglion cells and the effect on mast cells is indirectly mediated by neuropeptides. Carboxymethylation of histidine residues of SEB caused a complete loss of emetic and skin sensitizing activity without changing the immunological specificity, e.g., T cell stimulating activity. An anti-idiotype monoclonal antibody against the combining site of an anti-SEB monoclonal antibody had no enterotoxic activity but can inhibit the enterotoxic activity, e.g., emetic response and diarrhea of a 10,000 molar excess of SEB. Anti-idiotype antibody also inhibited immediate-type skin reactions as well. The anti-idiotype antibody and carboxymethylated enterotoxins may be useful tools to protect against the enterotoxin induced intestinal toxicity.

It is now recognized that various naturally occurring surface molecules, viruses and peptides may bear a striking sequence homology to the Staphylococcal enterotoxins to account for their superantigenic properties. Examples of these include the mammary tumor virus, minor lymphyocyte stimulating loci, naturally occurring heat shock proteins, as well as numerous species of mycoplasma and mycobacterium. It is conceivable that these sequences with superantigenic properties could exert powerful antitumor effects identical to the native enterotoxins and therefore be useful in this application.

Therefore, it could be predicted that peptides of the whole enterotoxin molecule can produce biologically active effects and reliably reproduce the in vivo tumoricidal activity of thee whole molecule while eliminating some of the toxic effects noted.

Moreover, it would be reasonable to assume that similar or increased tumoricidal effects could be accomplished with biologically active superantigen peptides, intact enterotoxins or superantigens alone or attached-to antigen presenting cells (class II MHC, HLA-DR) and incubated ex vivo with a random T cell population or one which may have been preenriched for the appropriate $V_\beta$ receptor. The activated T cell population with bound enterotoxin might then be reinfused into the host. Similar tumoricidal effects would be anticipated with enterotoxins or biologically active fragments infused into a host who has had an "organoid" (an enriched T lymphocyte organ) implanted on a biocompatible matrix and placed in a site in the host such as the abdominal cavity, adjacent to the liver or subcutaneously.

22. Antibodies to Enterotoxins

Antibodies specific for various enterotoxins have been documented to be present in the plasma of humans. Theoretically, these naturally occurring antibodies could neutralize injected-enterotoxins and accelerate their removal from the circulation. Alternatively, antibodies could combine with injected enterotoxins and create immunogenic antigen-antibody complexes.

To circumvent the presence of antibodies in the circulation, we have explored several methods of administering enterotoxins as follows: First, we have administered enterotoxins to several VX-2 bearing rabbits in adjuvant-vehicle form with slow release properties. Second, we have initiated a collaboration with Dr. Suyu Schu to evaluate the use of enterotoxins in an ex vivo mode, e.g., incubation of enterotoxins with T lymphocytes in the presence of IL-2 with resultant enrichment and expansion of T cells and subsequent reinfusion into the tumor bearing host. Such studies are presently underway.

Additionally, we envision the extracorporeal removal of antibodies of enterotoxins using immunoadsorption techniques with antibodies to enterotoxins immobilized on biocompatible solid supports over which plasma is perfused in an on-line fashion. Such immunoadsorption columns are now widely used and if this procedure is coupled with chemotherapy to suppress specific antibody production, a state of tolerance could be induced. Thus the plasma could be cleared of antibodies in advance of intravenous administration of the native toxins.

Non-immunogenic hybrid molecules or fragments of enterotoxins could be injected into antibody bearing hosts to neutralize existing circulating antibodies to the enterotoxins prior to administration of the native molecule. Such an approach is presently being tested in tumor bearing hosts.

Although the foregoing invention has been described in detail for purposes of clarity of understanding, certain modifications may be practiced within the scope of the appended claims. While the above findings apply to an experimental animal model, it should be recognized that the tumor used herein is an excellent model of human cancer. Therapeutic success in the canine model with PACC system (described in a series of patent applications, the latest of which is identified as Ser. No. 331,095), the forerunner of the present invention, was transferred to humans in which objective tumor regressions were obtained in four of the first five herein for rabbits with carcinoma is expected to be predictive of success when the compositions are applied to humans with spontaneous tumors as well.

TABLE 20

| | |
|---|---|
| | 10 20 30 40 50 |
| SEA | SEKSEEINEKDLRKKSELQGTALGNLKQIYYYNEKAKTENKESHDQFLQH |
| SEE | SEEINEKDLRKKSELQRNALSNLRQIYYYNEKAKTENKESDDQFLEN |
| SED | SVKEKELHKKSELSSTALNNMKHSYADKNPIIGENKSTGDQFLEN |
| SEB | ESQPDPKPDELHKSSKFTGL-MENMKVLYDDNHVSAINVK-SIDQFLYF |
| SEC1 | ESQPDPTPDELHKASKFTGL-MENMKVLYDDHYVSATKVK-SVDKFLAH |
| SEC3 | SQPDPTPDELHKSSEFTGT-MGNMKVLYDDHYVSATKVM-SVDKFLAH |
| SPE A | QQDPDPSQLHRSS-LVKN-LQNIYFLYEGDPVTHENVK-SVDQLLSH |
| SPE C | DSKKDISNV-KS-DLL-YAY-TIT-PYD--YKDCRVNFSTTHT-LNI |
| TSST-1 | ST-NDNIKDLLDWYS-SGSDTF-SNSEVLDN |
| ETA | EVSAEEIKKHEEKWNKYYGVNAFNLP---KELFSKVDEKDRQKYPYNTI |
| ETB | KEYSAEEIRKLKQK---------FEVPPTDKELYTHITDNARS--PYNSV |
| | 60 70 80 90 100 |
| SEA | TILFKGFFTDHSWYNDLLVDFDSKDIVDKY-KGKKVDLYGAYYGYQCAGG |
| SEE | TLLFKGFFTGHPWYNDLLVDLGSKDATNKY-KGKKVDLYGAYYGYQCAGG |
| SED | TLLYKKFFTDLINFEDLLINFNSKEMAQHF-KSKNVDVYPIRYSINCYGG |
| SEB | DLIYSIKDTKLGNYDNVRVEFKNKDLADKY-KDKYVDVFGANYYYQCYFS |
| SEC1 | DLIYNISDKKLKNYDKVKTELLNEGLAKKY-KDEVVDVYGSNYYVNCYFS |
| SEC3 | DLIYNISDKKLKNYDKVKTELLNEDLAKKY-KDEVVDVYGSNYYVNCYFS |
| SPE A | DLIYNVSG---PNYDKLKTELKNQEMATLF-KDKNVDIYGVEYYHLCYLC |
| SPE C | DTQ-KYRGKD--YY--ISSEM-SYEASQKFKRDDHVDVFGLFYILNSHTG |
| TSST-1 | SLGDM-RIKN-TDGSISLIIFPSPYYSPAFTKGEKVDLNTKRTKKSQHTS |
| ETA | GNVFVKGQTSATGVLIGKNTVLTNRHIAKFANGDPSKVSFRPSINTDDNG |
| ETB | GTVFVKGSTLATGVLIGKNTIVTNYHVAREAAKNPSNIIFTPAQNRDAEK |
| | 110 120 130 140 150 |
| SEA | T-----------PNKTACMYGGVTLHDNNRLTEEKKVPINL--WLDGKQN |
| SEE | T-----------PNKTACMYGGVTLHDNNRLTEEKKVPINL--WIDGKQT |
| SED | E-----------IDRTACTYGGVTPHEGNKLKERKKIPINL--WINGVQK |
| SEB | KKTNDINSHQTDKRKT-CMYGGVTEHNGNQL-DKYR-SITVRVFEDGKN- |
| SEC1 | SKD---NVGKVTGGKT-CMYGGITKHEGNHFDNGNLQNVLIRVYENKRN- |
| SEC3 | SKD---NVGKVTGGKT-CMYGGITKHEGNHFDNGNLQNVLIRVYENKRN- |
| SPE A | ENA-----------ERSACIYGGVTNHEGNHLEIPKK--IVVKVSIDGIQ- |
| SPE C | E----------------YIYGGITPAQNNKVNHKLLGNLFI--SGESQQN |
| TSST-1 | E-----------GTYIHFQISGVTNTE--KLPTPIELPLKVKVHG--KDS |
| ETA | NTE--TPYGEYEVKEILQEPFGAGVDLALIRLKPDQNGVSLGDKISPAKI |
| ETB | N-EFPTPYGKFEAEEIKESPYGQGLDLAIIKLKPNEKGESAGDLIQPANI |
| | 160 170 180 190 200 |
| SEA | TVPLETVKTNKKNVTVQELDPQARRYLQEKYNLYNSDVFDGKVQRGLIVF |
| SEE | TVPIDKVKTSKKEVTVQELDLQARHYLHGKFGLYNSDSFGGKVQRGLIVF |
| SED | EVSLDKVQTDKKNVTVQELDAQARRYLQKDLKLYNNDTLGGKIQRGKIEF |
| SEB | LLSFD-VQTNKKKVTAQELDYLTRHYLVKNKKLY--EFNNSPYETGYIKF |
| SEC1 | TISFE-VQTDKKSVTAQELDIKARNFLINKKNLY--EFNSSPYETGYIKF |
| SEC3 | TISFE-VQTDKKSVTAQELDIKARNFLINKKNLY--EFNSSPYETGYIKF |
| SPE A | SLSFD-IETNKKMVTAQELDYKVRKYLTDNKQLY--TNGPSKYETGYIKF |
| SPE C | --LNNKIILEKDIVTFQEIDFKIRKYLMDNYKIY--DA-TSPYVSGRIEI |
| TSST-1 | PLKYG-PKFDKKQLAISTLDFEIRHQLTQIHGLY----RSSDKTGGYWKI |
| ETA | GTSNDLKDGDKLELIGYPFDHKVNQMHRSEIELTTLSRGLRYYGFTVPGN |
| ETB | PDHIDIQKGDKYSLLGYPYNYSAYSLYQSQIEMFNDS---QYFGYTEVGN |
| | 210 220 230 240 250 |
| SEA | HTSTEPSVNYDLFGAQGQYSNY--LLRIYRDNKTINSE-NMHIDIYLYTS |
| SEE | HSSEGSTVSYDLFDAQGQYPDT--LLRIYRDNKTINSE-NLHIDLYLYTT |
| SED | DSSDGSKVSYDLFDVKGDFPE--KQLRIYSDNKTLSTE-HLHIDIYLYEK |
| SEB | IENE-NSFWYDMMPAPGDKFDQSKYLMMYNDNKMVDSK-DVKIEVYLTTK |
| SEC1 | IENNGNTFWYDMMPAPGDKFDQSKYLMMYNDNKTVDSK-SVKIEVHLTTK |
| SEC3 | IENNGNTFWYDMMPAPGDKFDQSKYLMMYNDNKTVDSK-SVKIEVHLTTK |
| SPE A | IPKNKESFWFDFFPEP-EFT-QSKYLMIYKDNETLDSN-TSQIEVYLTTK |
| SPE C | GTKDGKHEQIDLFDSPNEGT-RSDIFAKYKDNRIINMKNFSHFDIYL-EK |
| TSST-1 | TMNDGSTYQSDLSKKF-EYN-TEKPPINIDEIKTIEAEIN* |
| ETA | SGSGIFNSNGELVGIHSS--------------KVSHLDREHQINYGVGI |
| ETB | SGSGIFNLKGELIGIHSGKGGQHNLPIGVFFNRKISSLYSVDNT-FGDTL |

TABLE 20-continued

| | 260 |
|---|---|
| SEA | * |
| SEE | * |
| SED | * |
| SEB | KK* |
| SEC1 | NG* |
| SEC3 | NG* |
| SPE A | * |
| SPE C | * |
| TSST-1 | |
| ETA | GNYV-KRIINEKNE* |
| ETB | GNDLKKRAKIDK* |

What is claimed is:

1. A mammalian cell comprising an exogenous nucleic acid encoding a superantigen or a biologically active fragment of a superantigen that stimulates T cells via the T cell receptor $V_\beta$ chain, which superantigen or fragment is expressed in said cell, rendering said cell capable of stimulating antitumor immune reactivity in vitro or in vivo.

2. The cell of claim 1 that expresses MHC class II proteins.

3. The cell of claim 2, wherein said MHC class II proteins are HLA-DQ, HLA-DR, or HLA-DP molecules.

4. The cell of claim 1 that expresses adhesion molecules on its surface, which adhesion molecules augment the stimulation of T lymphocyte proliferation and tumoricidal activity when said cell is contacted with T lymphocytes.

5. The cell of claim 2 that expresses adhesion molecules on its surface, which adhesion molecules augment the stimulation of T lymphocyte proliferation and tumoricidal activity when said cell is contacted with T lymphocytes.

6. The cell of claim 5, wherein said MHC class II proteins are HLA-DQ, HLA-DR, or HLA-DP molecules.

7. The cell of claim 1, wherein said cell is a tumor cell.

8. The cell of claim 1, wherein said cell is an accessory cell.

9. The cell of claim 1, wherein said cell is an immunocyte.

10. The cell of claim 1, wherein said cell is a fibroblast.

11. The cell of claim 1, wherein said superantigen comprises a staphylococcal enterotoxin.

12. The cell of claim 11, wherein said staphylococcal enterotoxin is selected from the group consisting of SEA, SEB, $SEC_1$, $SEC_2$, $SEC_3$, SED, SEE, and SEF.

13. The cell of claim 1, wherein said superantigen comprises a streptococcal pyrogenic exotoxin.

14. The cell of claim 13, wherein said streptococcal pyrogenic exotoxin is selected from the group consisting of SPEA, SPEB, and SPEC.

15. The cell of claim 1, wherein said superantigen comprises a toxic shock associated toxin.

16. The cell of claim 15, wherein said toxic shock associated toxin is TSST1.

17. The cell of claim 1, wherein said superantigen comprises a *Staphylococcus aureus* exfoliating toxin.

18. The cell of claim 17, wherein said *Staphylococcus aureus* exfoliating toxin is selected from the group consisting of ETA and ETB.

19. The cell of claim 1, wherein said superantigen comprises a minor lymphocyte stimulating antigen.

20. The cell of claim 1, wherein said superantigen comprises a mycoplasma antigen.

21. The cell of claim 1, wherein said superantigen comprises a mycobacterial antigen.

22. The cell of claim 1, wherein said superantigen comprises a heat shock protein.

23. The cell of claim 1, wherein said superantigen comprises a stress peptide.

24. The cell of claim 1, wherein said superantigen is expressed on the surface of said cell.

25. The cell of claim 1, which, if natively not expressing MHC class II proteins, comprises a second exogenous nucleic acid that encodes an MHC class II protein that is expressed in said cell.

26. The cell of claim 25, wherein said MHC class II protein is an HLA-DQ, HLA-DR, or HLA-DP molecule.

27. The cell of claim 25 comprising a third exogenous nucleic acid that encodes an adhesion molecule expressed on the cell surface, which adhesion molecules augment the stimulation of T lymphocyte proliferation and tumoricidal activity when said cell is contacted with T lymphocytes.

28. The cell of claim 1 comprising a second exogenous nucleic acid that encodes an adhesion molecule expressed on the cell surface, which adhesion molecules augment the stimulation of T lymphocyte proliferation and tumoricidal activity when said cell is contacted with T lymphocytes.

29. The cell of claim 1 from a tumor-bearing host.

30. The cell of claim 29, wherein said host is a human.

* * * * *